United States Patent
Feiweier

(10) Patent No.: US 9,651,640 B2
(45) Date of Patent: May 16, 2017

(54) MAGNETIC RESONANCE SYSTEM AND METHOD FOR SLICE-SELECTIVE DETECTION AND CORRECTION OF INCORRECT MAGNETIC RESONANCE IMAGE DATA IN SLICE MULTIPLEXING MEASUREMENT SEQUENCES

(75) Inventor: Thorsten Feiweier, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 1290 days.

(21) Appl. No.: 13/602,751

(22) Filed: Sep. 4, 2012

(65) Prior Publication Data
US 2013/0057281 A1 Mar. 7, 2013

(30) Foreign Application Priority Data
Sep. 1, 2011 (DE) .................... 10 2011 082 009

(51) Int. Cl.
*G01R 33/565* (2006.01)
*A61B 5/055* (2006.01)
*G01R 33/483* (2006.01)

(52) U.S. Cl.
CPC .......... *G01R 33/4835* (2013.01); *A61B 5/055* (2013.01); *G01R 33/565* (2013.01); *G01R 33/56545* (2013.01); *G01R 33/56581* (2013.01)

(58) Field of Classification Search
USPC ........................... 324/300–322; 600/407–435
See application file for complete search history.

(56) References Cited

U.S. PATENT DOCUMENTS

| 5,422,572 A * | 6/1995 | Yao ..................... G01R 33/4835 324/309 |
| 6,853,188 B2 | 2/2005 | Feinberg et al. | |
| 7,224,165 B2 * | 5/2007 | Feiweier ............ G01R 33/5659 324/309 |

(Continued)

FOREIGN PATENT DOCUMENTS

JP 2008099889 A 5/2008

OTHER PUBLICATIONS

"Simultaneous Z-Shim Method for Reducing Susceptibility Artifacts With Multiple Transmitters," Deng et al., Magnetic Resonance in Medicine, vol. 61 (2009), pp. 255-259.

(Continued)

*Primary Examiner* — Melissa Koval
*Assistant Examiner* — Tiffany Fetzner
(74) *Attorney, Agent, or Firm* — Schiff Hardin LLP

(57) ABSTRACT

In a magnetic resonance (MR) method system for slice-selective detection and correction of incorrect magnetic resonance data, a first acquisition sequence is implemented to acquire MR data from a first slice of the examination subject that is associated with a chronologically first coherence curve of the magnetization; a second acquisition sequence is implemented to acquire MR data from a second slice of the examination subject that is associated with a chronologically second coherence curve of the magnetization. In slice multiplexing measurement sequences that are characterized by the simultaneous use of the transverse magnetization of the first and second slice within the first and second acquisition sequences slice-selective errors can be detected and corrections made.

41 Claims, 9 Drawing Sheets

(56) References Cited

U.S. PATENT DOCUMENTS

| | | | |
|---|---|---|---|
| 8,941,381 B2* | 1/2015 | Feinberg | G01R 33/4835 |
| | | | 324/307 |
| 2002/0167319 A1 | 11/2002 | Ikezaki | |
| 2005/0194974 A1* | 9/2005 | Feiweier | G01R 33/5659 |
| | | | 324/309 |
| 2007/0007960 A1 | 1/2007 | King et al. | |
| 2008/0258723 A1 | 10/2008 | Abe | |
| 2009/0085563 A1 | 4/2009 | Bito et al. | |
| 2009/0115794 A1 | 5/2009 | Fukuta | |
| 2010/0259260 A1 | 10/2010 | Lee et al. | |
| 2010/0286802 A1 | 11/2010 | Feiweier et al. | |
| 2011/0234221 A1 | 9/2011 | Feiweier | |
| 2012/0056620 A1* | 3/2012 | Feinberg | G01R 33/4835 |
| | | | 324/309 |
| 2013/0057280 A1* | 3/2013 | Feiweier | G01R 33/4835 |
| | | | 324/309 |
| 2013/0057281 A1* | 3/2013 | Feiweier | G01R 33/4835 |
| | | | 324/309 |

OTHER PUBLICATIONS

"Simultaneous Echo Refocusing in EPI," Feinberg et al., Magnetic Resonance in Medicine, vol. 48 (2002), pp. 1-5.

"Use of Multicoil Arrays for Separation of Signal from Multiple Slices Simultaneously Excited," Larkman et al., Journal of Magnetic Resonance Imaging, vol. 13 (2001), pp. 313-317.

"Concomitant Field Terms for Asymmetric Gradient Coils: Consequences for Diffusion, Flow, and Echo-Planar Imaging," Meier et al., Magnetic Resonance in Medicine, vol. 60 (2008), pp. 128-134.

"Efficient Design of Pulses with Trapezoidal Magnitude and Linear Phase Response Profiles," Pickup et al., Magnetic Resonance in Medicine, vol. 38 (1997), pp. 137-145.

"SIMA: Simultaneous Multislice Acquisition of MR Images by Hadamard-Encoded Excitation," Souza et al., Journal of Computer Assisted Tomography, vol. 12, No. 6 (1988), pp. 1026-1030.

"Wideband MRI: A New Dimension of MR Image Acceleration," Wu et al., Proc. Intl. Soc. Mag. Reson. Med., vol. 17 (2009), p. 2678.

"TE Interleaving: New Multisection Imaging Technique," Bishop et al., Journal of Magnetic Resonance Imaging, vol. 1 (1991), pp. 531-538.

"Multiplexed Echo Planar Imaging for Sub-Second Whole Brain FMRI and Fast Diffusion Imaging," Feinberg et al., PLoS one, vol. 5, Issue 12 (2010), e15710, pp. 1-11.

"Simultaneous Multislice Imaging With Slice-Multiplexed RF Pulses," Lee et al., Magnetic Resonance in Medicine, vol. 54 (2005), pp. 755-760.

* cited by examiner

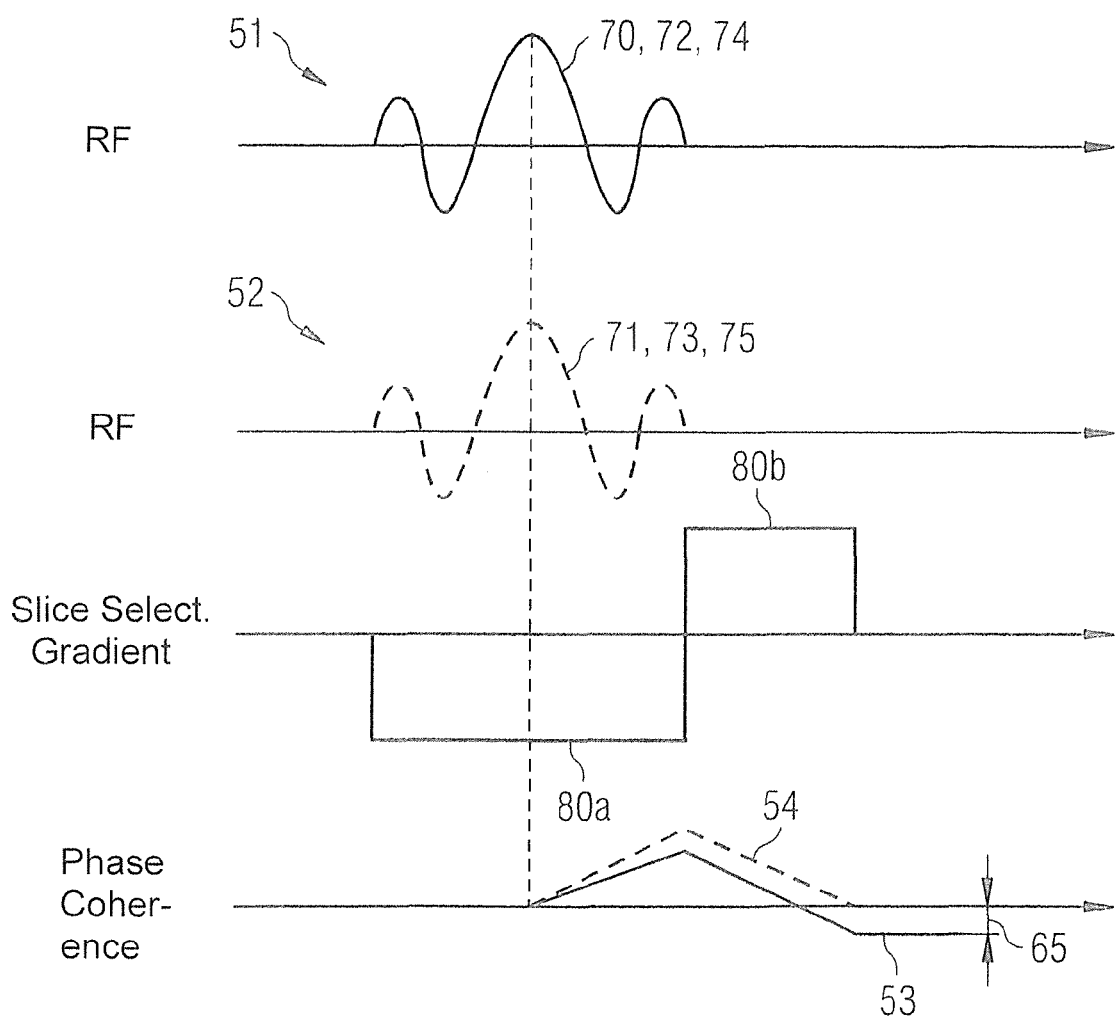

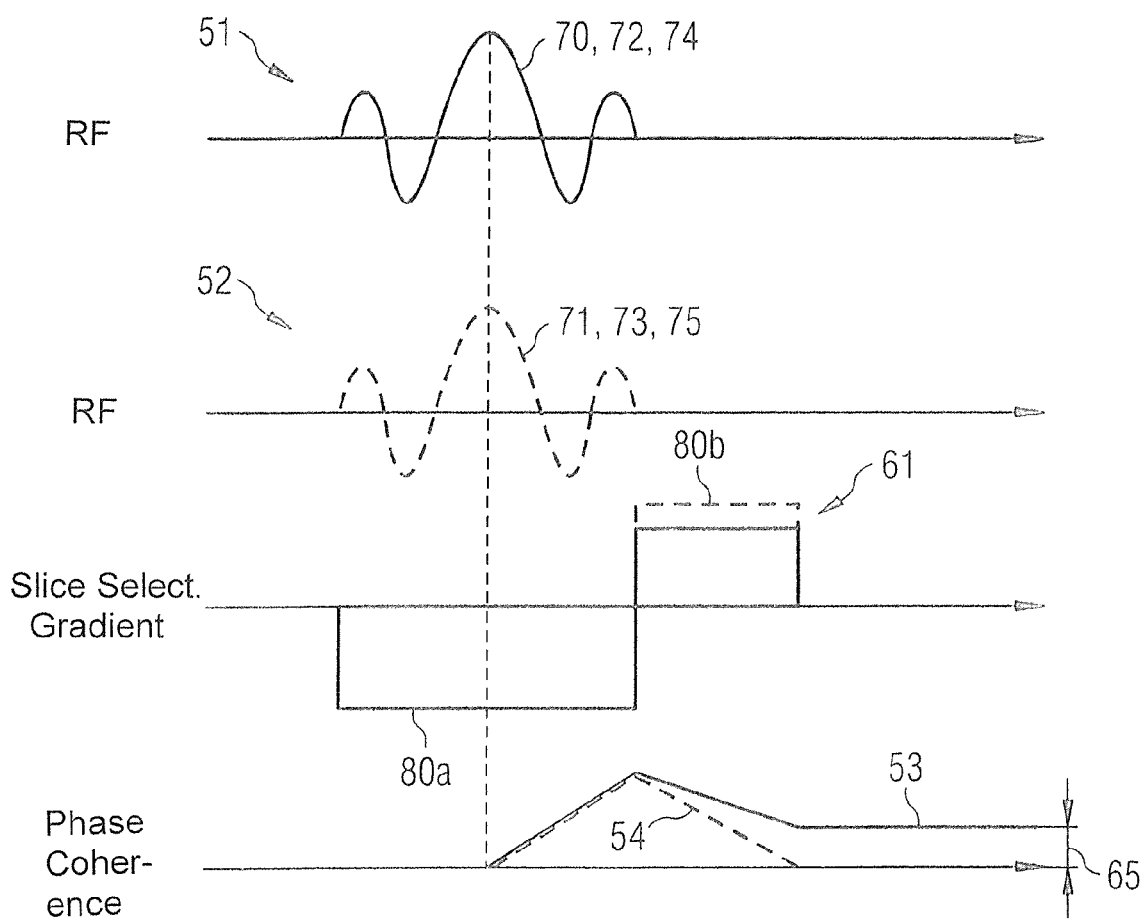

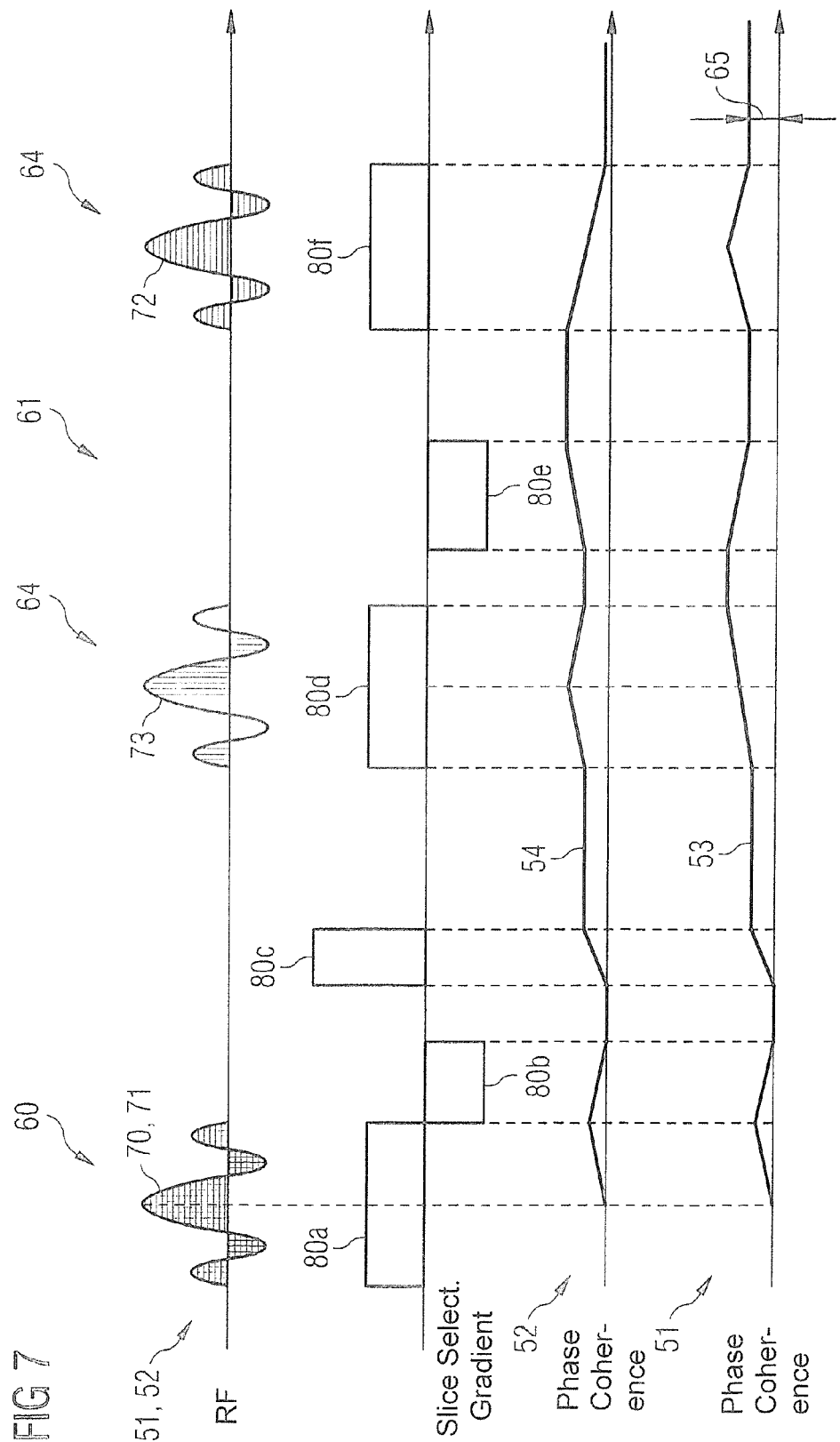

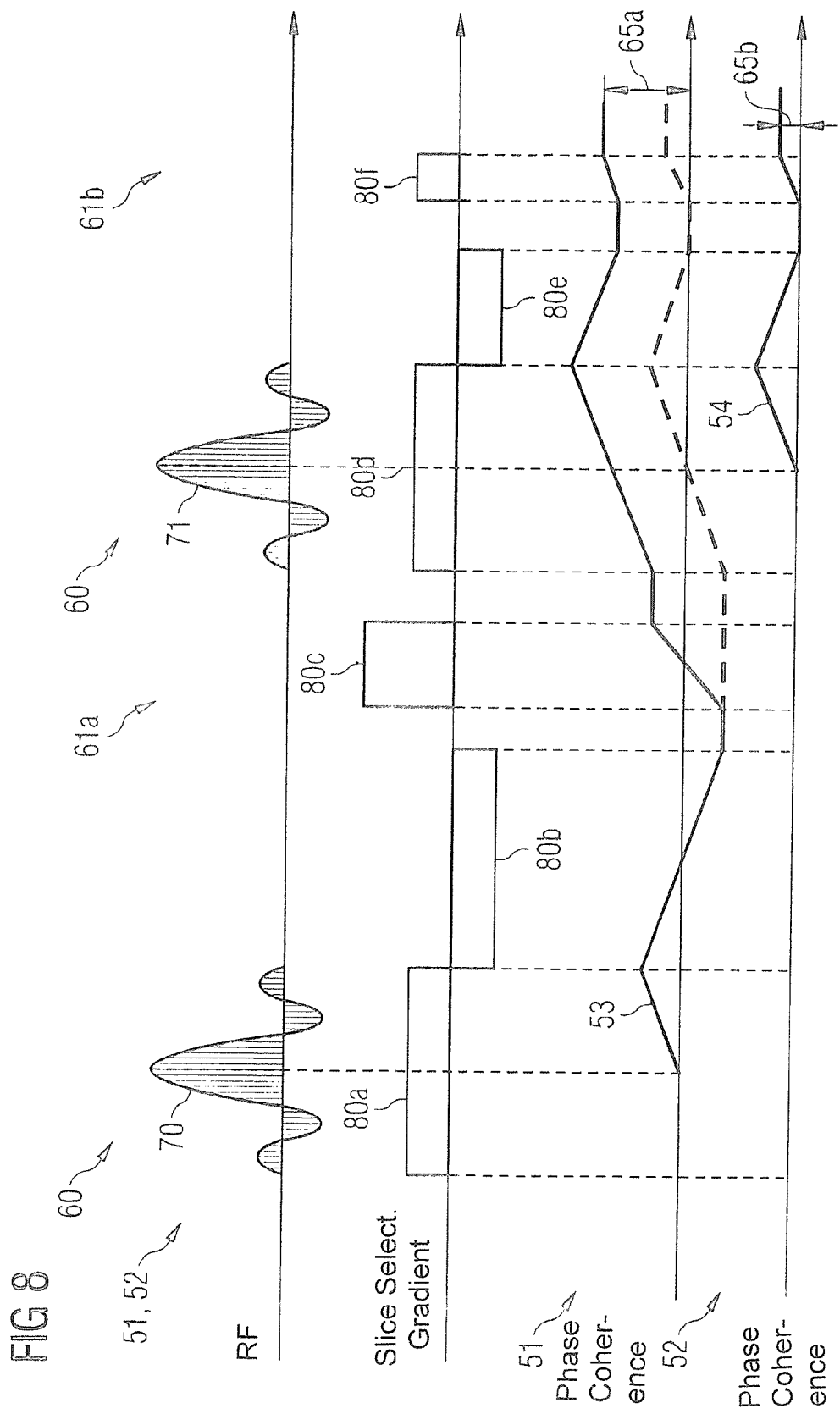

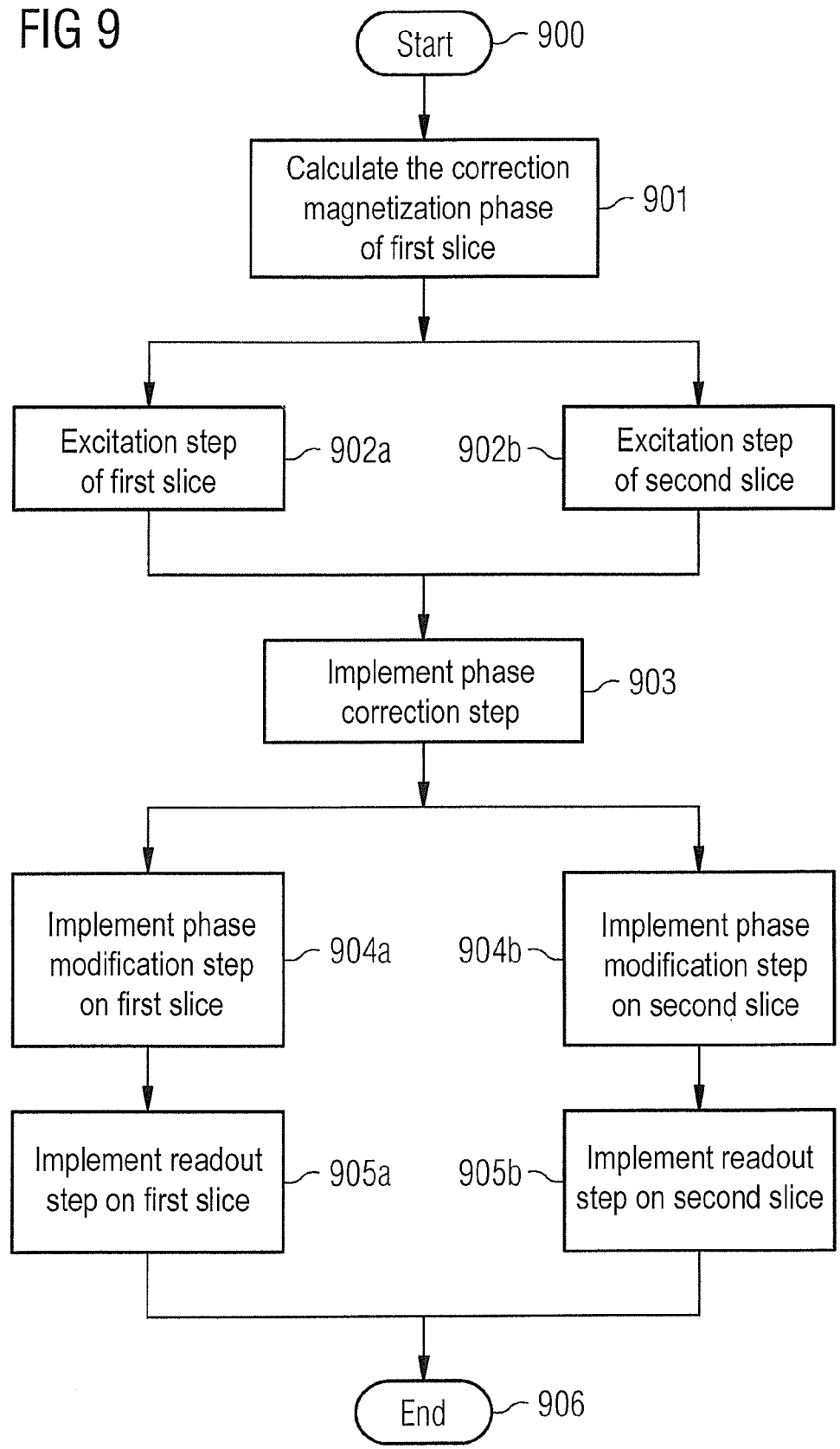

MAGNETIC RESONANCE SYSTEM AND METHOD FOR SLICE-SELECTIVE DETECTION AND CORRECTION OF INCORRECT MAGNETIC RESONANCE IMAGE DATA IN SLICE MULTIPLEXING MEASUREMENT SEQUENCES

BACKGROUND OF THE INVENTION

Field of the Invention

The invention concerns a method for slice-selective detection and correction of incorrect magnetic resonance (MR) image data in slice multiplexing measurement sequences, and a magnetic resonance system designed to implement such a method. In particular, the present invention concerns the individual detection and correction in individual slices given otherwise parallel imaging.

Description of the Prior Art

Magnetic resonance tomography is an imaging technique that is used for examination and diagnosis in many fields of medicine. The physical effect of nuclear magnetic resonance forms the basis. To acquire MR signals, a static basic magnetic field is generated in the examination region at which the nuclear spins (the magnetic moments) of the atoms in the examination subject align. The nuclear spins can be deflected or excited out of the aligned position (i.e. the idle state) or a different state by radiating radio-frequency pulses. During the relaxation back into the idle state, a decay signal is emitted that can be inductively detected by one or more reception coils.

The phase evolution of the spin system of a slice is described by the coherence curve (progression). If the spins of a spin system of a specific slice all have an identical phase position, this is described by a disappearing dephasing of the coherence curve. A signal can be detected since no destructive interference exists between the signals of various spins of different phase.

By applying a slice selection gradient upon radiation of the radio-frequency pulses, nuclear spins are excited only in a slice of the examination subject in which the resonance condition due to the local magnetic field strength is satisfied. An additional spatial coding can take place by the application of at least one phase coding gradient, and a frequency coding gradient can be activated during the readout. It is thereby possible to acquire MR exposures of multiple slices of an examined person. By means of suitable presentation methods it is possible to provide a 3-dimensional (3D) image of a specific region of the examined person for diagnosis.

In the clinical environment there is always a quest for faster MR acquisitions, in particular 3D acquisitions. MR measurement sequences to generate MR exposures can be optimized in this regard. In particular, MR sequences in which images are acquired simultaneously from multiple slices within the scope of multiple acquisition sequences (i.e. sequences as slice multiplexing measurement sequences) lend themselves to this. In general, slice multiplexing measurement sequences can be characterized by a transverse component of the magnetization of at least two slices being specifically used simultaneously for the imaging process, at least during a portion of the measurement. The use of magnetization for the imaging process can mean the simultaneous excitation or deflection of the magnetization, the simultaneous dephasing and rephasing (by gradient fields, for example) or also the simultaneous readout of the magnetization. In contrast to this, in the established multislice imaging, the signal of at least two slices is acquired in alternation, i.e. completely independently of one another and with a correspondingly longer measurement time (what are known as "interleaved" measurement sequences). This is essentially intended to produce a mere relaxation of the magnetization of one slice during the excitation of an additional slice, which does not directly contribute to the imaging process.

Various slice multiplexing measurement sequences are known. For example, given simultaneous excitation of the magnetization and/or detection of an MR signal the addressing of the various slices can take place via a phase coding (what is known as "Hadamard" coding; see in this regard S. P. Souza et al. in J. Comput. Assist Tomogr. 12 (1988) 1026) or a frequency coding (what is known as broadband data acquisition; see in this regard E. L. Wu et al. in Proc. Intl. Soc. Mag. Reson. Med. 17 (2009) 2678).

Furthermore, there are MR measurement sequences that use multiple radio-frequency coils to differentiate various slices. With knowledge of the spatial acquisition characteristic of the different radio-frequency coils, the simultaneously acquired data can be separated by means of suitable computing operations. Such methods are known under the names SENSE, GRAPPA or SMASH, for example, as described in D. J. Larkman et al. in J. Mag. Res. Imag. 13 (2001) 313.

An additional measurement sequence is based on the short temporal separation of the signal excitation steps and the signal detection steps. However, the gradient pulses are suitably switched so that at the same time the coherence curve of the transversal magnetization or the dephasing of the spin systems of different slices can be varied (simultaneous echo refocusing, as described in D. A. Feinberg et al. in Magn. Reson. Med. 48 (2002) 1.)). Images of both slices can be generated as is customary from the MR image data, which are acquired with hardly any temporal separation.

In the acquisition of MR image data, systematic and statistical errors in the acquisition process can generate artifacts in the MR image data. Incorrect MR image data normally cannot be used for medical diagnostics. Therefore there are numerous correction methods for the reduction of image artifacts that can be applied to single slice imaging or the established multislice imaging, in which the signals of multiple slices are acquired completely independently of one another.

For example, such correction methods concern the correction of phase errors caused by accompanying Maxwell fields. Ideal magnetic field gradients are physically unrealizable. A deviation of the spatial dependency of the magnetic field gradients relative to the linear case follows from Maxwell's equations. A correction of this Maxwell field due to phase errors is possible on the basis of calculated correction parameters. In particular, it is desirable to already apply the phase corrections slice-selectively during the acquisition process. An artifact formation due to incorrect MR data can then already be avoided during the acquisition process.

Furthermore, it is possible to correct segment-dependent phase errors. Due to statistical measurement errors, individual segments of the MR image data can exhibit phase errors. In particular, such segment-dependent phase errors are slice-specific. For example, in the literature the image artifacts produced by segment-dependent phase errors are known by the term "Nyquist ghosts". Such phase errors or image artifacts can be computationally compensated via the measurement of reference phases. However, it is must be ensured that the detected reference data are slice-specific.

The possibilities of correction or detection of incorrect MR image data are very limited in slice multiplexing measurement sequences. In particular, due to the high degree of parallelism of the acquisition sequences of different slices there is hardly any possibility to individually affect individual slices or acquire individual slice-specific data. Correction methods that are only implemented in image space (i.e. already take place after the measurement and after separation of the slice image previously acquired in parallel) do not have the same efficiency as corrections that are applied during the measurement process itself or during the measurement sequence.

From DE 10 2009 020 661 A1 a method is known that achieves an optimally slice-specific optimization of MR measurement sequences or, respectively, a correction of incorrect MR data by means of a suitable establishment of the active volume as a set union of the volumes of all simultaneously acquired slices. However, given increasing spatial separation of the measured slice a correction implemented in such a manner suffers from a degradation since the approximation of an individual active volume no longer applies given an increasing spatial separation.

SUMMARY OF THE INVENTION

An object of the invention is to provide methods and devices that enable slice-specific corrections of incorrect MR data to be implemented in slice multiplexing measurement sequences. In particular, an object of the invention is to provide methods and devices that enable individual slices to already be individually affected in the acquisition process so as to correct incorrect MR data, as well as to enable individual items of k-space information of the slices to be acquired in order to make slice-specific corrections based on these items of information.

In a method in accordance with the invention for slice-selective detection of incorrect MR image data in slice multiplexing measurement sequences, in which at least two slices of an examination subject are imaged, the following steps are implemented. A first acquisition sequence is executed to acquire MR data from a first slice of the examination subject that is associated with a chronologically first coherence curve of the magnetization. A second acquisition sequence is executed to acquire MR data from a second slice of the examination subject that is associated with a chronologically second coherence curve of the magnetization.

Furthermore, according to the invention a slice-selective correction data acquisition is executed to acquire MR signals only from the first slice for correction purposes, wherein the first and second acquisition sequence temporally overlap at least in part such that the magnetization of the at least two slices is used simultaneously at one point in time (at least).

Furthermore, according to the invention at least one correction assistance step is executed to suppress a signal contribution of the second slice during the correction data acquisition step and to reestablish the first and second coherence curves after the correction data acquisition step.

The coherence curve designates the temporal evolution of the dephasing of the magnetization, thus the dephasing of the spin system. For example, after the generation of a magnetic field component that is transverse to the basic field the individual transverse magnetic field components are aligned identically and therefore have an identical phase. Here the coherence curve has a disappearing dephasing. With increasing progression of time, the various spins assume different phase positions, meaning that the coherence curve dephases.

Given measurement sequences of the established multislice imaging ("interleaved" measurement sequence), the spin systems of the individual slices are affected entirely in isolation and independently of one another. In spite of the possibly interleaved design of the MR measurement sequence (i.e. a partially parallel implementation of the measurement sequence), the actions on the transverse magnetization take place independently of one another. Slice multiplexing measurement sequences as are employed in the present invention are to be differentiated relative to this. In slice multiplexing measurement sequences, the transversal magnetization of multiple slices simultaneously is used for the MR imaging process.

A method according to the invention has the advantage that MR signals from only one slice can be acquired during the correction data acquisition step. The acquisition of MR signals from (for example) the first slice can take place for correction purposes. For example, phase correction parameters can be acquired with which different background phase curves in different segments of MR data can be corrected. Using the acquisition of correction data in the slice-selective correction data acquisition step, it is possible to determine the background phase curve slice-selectively, and thus to achieve a high precision in the correction of incorrect MR data due to slice-specific, segment-dependent background phase curves. The correction data acquisition step is not limited to the acquisition of data to correct phase curves. Other MR data can also be acquired for correction purposes.

In order to be able to acquire slice-specific MR data in slice multiplexing measurement sequences, it should be ensured that no additional slices, other than the selected slice, contribute to the acquired signal during the MR data acquisition. This can be achieved by suppressing the signal contribution of the second slice, for example by affecting the second coherence curve. For this, after the correction data acquisition step the second coherence curve should be reestablished. This ensures that the additional course of the MR measurement sequence is not affected by the preceding correction data acquisition step.

It is possible to use an MR measurement sequence according to the invention for the imaging of more than two slices. The aforementioned features can be applied to the acquisition of MR data from three or more slices.

The correction assistance step can include at least one gradient field that introduces a correction assistance phase such that the second coherence curve has a dephased coherence curve during the correction data acquisition step. Given a dephased second coherence curve, the spins of the second slice have respectively different phase positions. Due to the different phase position of the various spins, no signal can be detected from the second slice because of destructive interference of the spins of the spin system. However, if the spins of the spin system of the first slice have a non-dephased coherence curve (meaning that the spins are in phase) at the same point in time (i.e. during the correction data acquisition step), a signal can be acquired from the first slice. In particular, the gradient fields are suitable to introduce a correction assistance phase within the scope of the correction assistance step. The correction assistance phase can be used to specifically dephase or rephase the respective coherence curves.

Furthermore, it is possible for the gradient fields to have a nonlinear spatial curve and for the correction assistance phase to be slice-specific. It can be advantageous if the impressed phase to achieve a dephasing or rephasing during the correction assistance step is slice-specific. For example, the coherence curve of the first slice can be specifically rephased while the coherence curve of the second slice is dephased simultaneously and without additional time loss.

For example, nonlinear gradient fields can be generated in that an additional, switchable field coil is provided with nonlinear field curve. The correction assistance phase impressed by a nonlinear magnetic field gradient is dependent on the position of the respective slice along the direction of the nonlinearity of the magnetic field gradient. For example, a magnetic field gradient can be used that is described by a quadratic function. In particular via suitable dimensioning of the linear and quadratic portion it can hereby achieved that the area near the relevant slices of the curve of the magnetic field gradient can be described in good approximation via a linear function. This represents an easily controllable temporal evolution of the coherence curve over the entire slice thickness. The effective active magnetic field gradient or the effective impressed correction assistance phase is then slice-specific. The coherence curves of two or more slices can be rephased or dephased simultaneously in this way.

It can be advantageous for the at least one correction assistance step to impress a correction assistance phase by a suitable amplitude and/or phase modulation of at least one RF pulse, for example an excitation pulse or refocusing pulse. In the literature, for example, such a method is known (S. Pickup and M. Popescu in Magnetic Resonance in Medicine 38 (1997) 137-145) that allows the dependency of the phase (the coherence curve) impressed by the pulse on the magnetization to be determined via an RF pulse. After application of the RF pulse, a rephased coherence curve can already be achieved by specific design of the RF pulses with an amplitude and/or phase modulation. This causes the first and second coherence curves to have such different temporal evolution that the second coherence curve is dephased at the point in time of the correction data acquisition step.

Particularly in consideration of slice multiplexing measurement sequences, this has the advantage that the high degree of parallel action on the spin systems of different slices does not need to be reduced through a partially serial effect on the slices. For example, it is possible to implement the excitation step in parallel for two slices, i.e. to simultaneously implement radio-frequency excitation pulses. However, at the same time the coherence curves can be affected individually in order to produce an effect described in the preceding.

Furthermore, the acquisition sequences can include an excitation step to deflect the magnetization out of the idle state, a phase modification step to dephase and rephase the magnetization, and a readout step to read out a signal of the magnetization in a signal detection time.

An acquisition sequence typically includes the deflection of the magnetization out of the idle state, i.e. the generation of a transverse magnetization component. The idle state is defined by the static basic magnetic field. After generating a transversal magnetization component, by means of a phase modification step the coherence curve of the magnetization is made to change as a function of time. The phase modification step can have the effect that a signal of the magnetization is generated after a certain time period. This signal of the magnetization can be detected in the readout step and allows conclusions about the magnetic parameters in the detection region.

It is possible for at least one of the excitation step and the phase modification step to include a radio-frequency pulse. The deflection of the magnetization out of the idle state can occur dynamically. An additional radio-frequency pulse can be applied during the phase modification step in order to invert the direction of the dephasing of a spin system, for example. Such a method is also known as a spin echo method.

Furthermore, the phase modification steps can include radio-frequency refocusing pulses to generate a spin echo. RF refocusing pulses produce an inverted dephasing of the transversal magnetization of a spin system. The application of an RF pulse can cause the dephasing spins to generate a signal in the form of a spin echo.

This has the advantage that, in a sequence of the different phase modification steps occurring with a time offset, the evolution of the first and second coherence curves can be achieved with the correction assistance step at different points in time with radio-frequency refocusing pulses. For example, a gradient field is applied to introduce a correction assistance phase before a refocusing pulse, the correction assistance phase being added to the dephasing of the coherence curve. In contrast, if a gradient field is applied to introduce a correction assistance phase chronologically after a radio-frequency refocusing pulse during the phase modification step, the correction assistance phase is subtracted from the phase position of the coherence curve. Given a time separation of the phase modification steps, the spin systems of the different slices can be individually affected.

However, it is also possible for the phase modification step to include no radio-frequency pulse. A dephasing and subsequent rephasing of the spin system is also possible by means of gradient fields (what is known as a "gradient echo method"). Gradient echo methods within the scope of slice multiplexing measurement sequences are known to those skilled in the art, as is discussed below.

Furthermore, the excitation step of the first slice and the correction data acquisition step can occur before the excitation step of the second slice. If the excitation step of the first slice and the correction data acquisition step occur before the excitation step of the second slice, this has the advantage that the spin system of the second slice is still found in the idle state at the point in time of the correction data acquisition step. This means that no transverse magnetization of the second slice which could contribute to a signal is present during the correction data acquisition step. This means that only signals from the first slice can thus be acquired during the correction data acquisition step.

It is also possible for the excitation step of the first slice and the correction data acquisition step to occur after the excitation step of the second slice, and for the correction assistance step to occur before the correction data acquisition step ensures dephasing of the signal of the second slice, so that after the correction data acquisition step the signal of the first and second slices rephases. If the correction data acquisition step occurs after the excitation step of the second slice, this means that a final transversal magnetization of the spin system of the second slice is already present at the point in time of the correction data acquisition step. In such a case it must be ensured that the second coherence curve has a dephasing at the point in time of the correction data acquisition step. Otherwise, a signal from the second slice could also be present during the correction data acquisition step. After the correction data acquisition step, the correction assistance step accordingly ensures that the coherence curves of the first and second slice are rephased. For example this means that, relative to the coherence curves of the spin system of the first and second slice, a state is established that is identical to the state that would have been present without the presence of a correction data acquisition step. This in particular ensures that conventional MR measurement sequences can subsequently be further implemented according to slice multiplexing. It is thus not necessary to adapt the measurement sequences to the particular conditions because of the presence of a correction data acquisition step.

It is possible for the acquisition sequences to include a simultaneous echo refocusing sequence, and for the readout steps for all acquisition sequences to occur with a time offset in the signal detection time period.

A slice multiplexing measurement sequence based on simultaneous echo refocusing is known in the literature from D. A. Feinberg et al. in Magn. Reson. Med. 48 (2002) 1. The transverse magnetization of two slices is simultaneously affected, for example. In the case of the simultaneous echo refocusing, this occurs such that both the excitation pulses and the signal detection occur with a slight time offset. However, the switched phase coding gradients are used in order to specifically simultaneously affect the transversal magnetization of both slices or to simultaneously use the transversal magnetization for the MR imaging process. Therefore, in such a method it is not simply possible to individually affect the transversal magnetization of one of the various slices.

However, it is also possible for the readout steps for all acquisition sequences to occur simultaneously in the signal detection time period. The simultaneous implementation of the readout steps in the signal detection time period has the advantage that other specific slice multiplexing measurement sequences can be implemented. For example, the signal of the different slices can be differentiated in frequency or phase space. The measurement time can be reduced by the parallel implementation of the data acquisition.

It is also possible for the excitation steps to at least partially temporally overlap. Given a complete temporal overlapping of the excitation steps—for example in the form of radio-frequency (RF) pulses—the time duration required for measurement is minimized. In contrast, given a complete time synchronization of various RF pulses a greater peak RF power is required in comparison to sequentially implemented RF pulses. This is frequently undesirable since a high peak RF power is accompanied by a higher specific absorption rate (SAR) of a patient. Conversely, given a partial temporal overlap of RF pulses a compromise is achieved between shorter measurement time and lower peak RF power. The peak RF power can be reduced while the measurement time is further shortened relative to sequential implementation.

It is possible for the excitation steps of the acquisition sequences to at least partially temporally overlap. A partial temporal overlap of the excitation steps—in particular of the exciting radio-frequency pulses—has the advantage that the required RF pulse amplitude is reduced given the same deflection of the magnetization. If two radio-frequency (RF) pulses are applied in parallel, in general the required RF power is greater than in the case of a serial application. However, even with only a partial temporal overlap both the measurement time and the required RF power can be reduced.

Given a parallel implementation of the excitation or detection, for example, the various signals can be differentiated by means of the phase or frequency of the associated signal. A phase or frequency coding of the various slices has the advantage that both slices can be simultaneously affected in parallel during one and the same time period. This has the advantage that the measurement time duration is correspondingly shortened.

An additional possibility to differentiate between various slices is to use multiple RF coils to implement the acquisition sequence. If multiple RF coils are used to implement acquisition sequences, this has the advantage that various RF coils have different spatial sensitivities. Given knowledge of the various spatial sensitivities of the multiple measurement coils, the signal of individual slices can be extracted and separated from the multiple data sets. Methods of parallel imaging (for example GRAPPA, SMASH or SENSE) are hereby known in the literature. Even when multiple measurement coils are used for the acquisition of MR data in various acquisition sequences, a higher degree of parallelism can be achieved via simultaneous action on the transversal magnetization of various slices.

It is also possible for the excitation steps or phase modification steps of the various acquisition sequences occur with a time offset. It can be advantageous for the slice multiplexing measurement sequences to be varied such that the various slices are affected with a time offset at least during a portion of the acquisition sequences (for instance during the phase modification step). If the various slices are affected with a time offset, this has the advantage that the coherence curves of the various slices have a different phase evolution at different points in time.

The above object also is achieved by a magnetic resonance system in accordance with the invention designed for slice-selective detection of incorrect MR image data in slice multiplexing measurement sequences, in which at least two slices of an examination subject are depicted. The magnetic resonance system has a pulse sequence controller that is configured to operate an MR data acquisition device (scanner) to execute a first acquisition sequence to acquire MR data from a first slice of the examination subject that is associated with a chronologically first coherence curve of the magnetization; and to execute a second acquisition sequence to acquire MR data from a second slice of the examination subject that is associated with a chronologically second coherence curve of the magnetization. The magnetic resonance system has a computer that is configured to implement a slice-selective correction data acquisition in order to acquire MR signals only from the first slice for correction purposes, with the first and second acquisition sequences at least partially temporally overlapping, such that the respective magnetizations of the at least two slices are used simultaneously at one point in time. The pulse sequence controller is furthermore configured to implement the following step: at least one correction assistance to suppress a signal contribution of the second slice during the correction data acquisition step and to reestablish the first and second coherence curves after the correction data acquisition.

With a magnetic resonance system of such a design, advantageous and desired effects can be achieved that correspond to those described above in relation to the method.

According to a further aspect of the invention, a method is provided for slice-selective correction of incorrect MR image data in slice multiplexing measurement sequences in which at least two slices of an examination subject are depicted, wherein a first acquisition sequence is executed to acquire MR data from a first slice of the examination subject that is associated with a chronologically first coherence curve of the magnetization, a second acquisition sequence is executed to acquire MR data from a second slice of the examination subject that is associated with a chronologically second coherence curve of the magnetization, with the first and the second acquisition sequences at least partially temporally overlap so that the respective magnetizations of the at least two slices are used simultaneously at one point in time (at least).

This embodiment of the invention furthermore includes implementing at least one correction step to impress a slice-specific correction magnetization phase for targeted modification of the first coherence curve while maintaining the second coherence curve.

As already described, compared to conventional methods of multislice imaging ("interleaved" measurement sequences), slice multiplexing measurement sequences are characterized by the transverse magnetization of multiple slices being affected simultaneously and jointly at at least one point in time. This means that the transverse magnetization of multiple slices is simultaneously used for MR imaging.

The impression of a slice-specific correction phase can have the advantage of already correcting or compensating for incorrect phase positions of a signal during the acquisition process. It is decisive that the incorrect phase positions can be slice-specific. A phase error of the first slice thus can be different from a phase error of the second slice. A global correction of the phase by the impression of one and the same correction magnetization phase on all slices participating in the slice multiplexing measurement sequence lacks the desired effect of a phase correction. According to the invention, however, a correction magnetization phase can be impressed slice-specifically. In particular, it is possible for a correction phase to already have been impressed beforehand on the second coherence curve.

There are numerous causes of incorrect phase positions. Maxwell phase errors are one possibility. Maxwell phase errors are due to the fact that ideal gradient fields—i.e. purely linear dependencies of a specific component of the magnetic field strength depending on the position—do not form a solution to Maxwell's equations, i.e. the fundamental equations of the electromagnetic field. Spatially dependent (and therefore in particular slice-specific) corrections are necessary. These corrections can be calculated so that, in principle, phase errors due to the Maxwell field can already be corrected during the acquisition sequence on the basis of the calculated correction magnetization phases.

According to the present invention, this can be achieved by a correction step that impresses a slice-specific correction magnetization phase. Moreover, the second coherence curve is not modified, such that the acquisition sequence can be continued without interruption. Therefore it is not necessary to take additional precautions after the correction step. Known slice multiplexing measurement sequences can be applied.

It is possible for the acquisition sequences to each include an excitation step to excite the magnetization, a phase modification step to dephase and rephase the magnetization, and a readout step to read out a signal of the magnetization in a signal detection time period. As described above, these steps can produce the generation of a signal of the magnetization.

It is possible for the acquisition sequences include a simultaneous echo refocusing sequence, and for the readout steps for all acquisition sequences to occur with a time offset in the signal detection time period. The advantages of an MR acquisition sequence according to simultaneous echo refocusing have already been explained above.

It is also possible for the readout steps for all acquisition sequences occur simultaneously in the signal detection time period. The advantageous effects have been explained in detail above.

For example, the various slices can be differentiated in terms of phase or frequency of the associated signal. It is also possible to use multiple coils to implement the acquisition. All of these methods allow data to be acquired at least partially in parallel or allow various slices to be slice-selectively affected at least partially in parallel, as explained above.

Furthermore, the excitation steps can at least partially temporally overlap. As described above, the required RF power can be reduced if the excitation steps partially temporally overlap.

It is also possible for the at least one correction step to include a radio-frequency pulse to deflect the spin system via suitable amplitude and/or phase modulation so that at least a portion of the correction magnetization phase is impressed during the application of the radio-frequency pulse.

As explained above, radio-frequency pulses can intrinsically provide a phase position of the coherence curve. The advantages described also apply to this embodiment of the invention.

The at least one correction step can include the application of a gradient field to impress at least a portion of the correction magnetization phase. As described above, the phase position of the coherence curve can be specifically implemented by a gradient field. The advantages described above apply to this embodiment.

The aforementioned gradient field preferably has a nonlinear spatial curve. A nonlinear gradient field enables different correction phases to be impressed given parallel application to various slices, described above.

As described above, the phase modification step can include radiation of a radio-frequency refocusing pulse, or the excitation step can include radiation of a radio-frequency excitation pulse, to achieve the same advantageous effects as described above.

It is for a first gradient field of the correction step to be applied before the radio-frequency refocusing pulse of the second acquisition sequence, and for a second gradient field of the correction step to be applied after the radio-frequency refocusing pulse of the second acquisition sequence. In this regard it can be advantageous for both gradient fields to be applied either before or after the RF refocusing pulse of the first slice. This has the advantage that the phase impressed by the gradient field of the correction step is respectively added with different algebraic sign to the phase position of the coherence curve of the second slice, respectively before and after the refocusing of the second slice. At the same time, the phase impressed on the first coherence curve has the same algebraic sign for the different gradient fields. In summary, different phases can be impressed respectively on the first and second coherence curves.

It is also possible for a first gradient field of the correction step to be applied before the radio-frequency excitation pulse of the second acquisition sequence, and for a second gradient field of the correction step to be applied after the radio-frequency excitation pulse of the second acquisition sequence. If a gradient field is applied before the radio-frequency excitation pulse of the second acquisition sequence, this has no effect on the second coherence curve. This is because no transverse magnetization of the second slice that could be dephased/rephased by the gradient field has yet been generated at the point in time of the application of the gradient field. Therefore it is possible—in particular given application of the gradient field before the excitation pulse of the second slice—to only affect the first coherence curve.

In this regard, it can be advantageous for the excitation step of the first slice and the correction step to take place before the excitation step of the second slice. Transverse magnetization then already exists in the first slice when the magnetization is still located in the idle state (no transverse magnetization) in the second slice. If the correction phase is implemented within the scope of the correction step, before the deflection of the magnetization of the second slice out of the rest phase, the first slice can be affected individually. The later coherence curve of the second slice remains untouched.

The above object also is achieved in accordance with the invention by a magnetic resonance system for slice-selective correction of incorrect MR image data in slice multiplexing measurement sequences, in which at least two slices of an examination subject are depicted, that has a pulse sequence controller that is configured to operate an MR data acquisition unit (scanner) to execute a first acquisition sequence to acquire MR data from a first slice of the examination subject that is associated with a chronologically first coherence curve of the magnetization, and to execute a second acquisition sequence to acquire MR data from a second slice of the examination subject that is associated with a chronologically second coherence curve of the magnetization, with the first and second acquisition sequence at least partially temporally overlapping such that the magnetizations of the at least two slices are used simultaneously at one point in time (at least), and to implement at least one correction step to impress a slice-specific correction magnetization phase for targeted modification of the first coherence curve while maintaining the second coherence curve.

The advantages described above with regard to other embodiments of the invention also apply to this embodiment.

BRIEF DESCRIPTION OF THE DRAWINGS

FIG. 5 schematically illustrates a slice multiplexing measurement sequence to impress a correction magnetization phase on the coherence curve of a first slice.

FIG. 6 schematically illustrates a slice multiplexing measurement sequence to impress a correction magnetization phase on the coherence curve of a first slice.

FIG. 7 schematically illustrates a slice multiplexing measurement sequence to impress a correction magnetization phase on the coherence curve of a first slice.

FIG. 8 schematically illustrates a slice multiplexing measurement sequence to impress a correction magnetization phase on the coherence curve of a first and second slice.

FIG. 9 is a flowchart of a further embodiment of a slice multiplexing measurement sequence to impress a correction magnetization phase.

DESCRIPTION OF THE PREFERRED EMBODIMENTS

Figure 1:
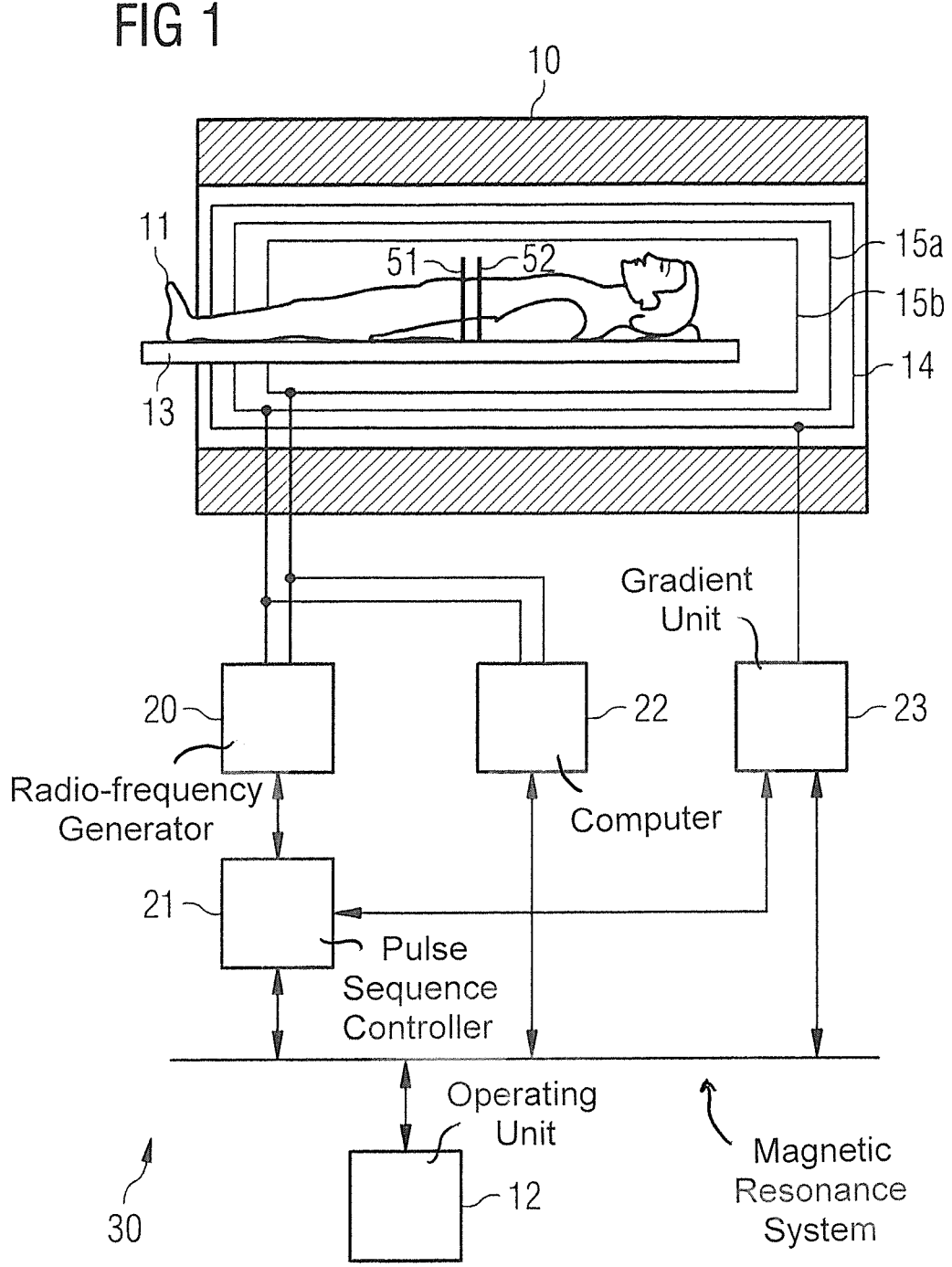
FIG. 1 schematically illustrates a magnetic resonance system of the present invention.

FIG. 1 schematically shows a magnetic resonance system 30 designed to acquire magnetic resonance (MR) data. The MR system can have multiple radio-frequency coils 15, 15b, but it is also possible for the MR system 30 to have only one radio-frequency coil. The MR system 30 furthermore has a magnet 10 that is suitable to generate a basic magnetic field. An examination subject—in the presented case an examined person 11—can be slid into the magnet 10 by a movable bed 13. To generate MR image data from a first slice 51 and second slice 52 that are oriented along the examined person 11, the MR system 30 furthermore has a gradient system 14 configured to provide magnetic field gradients in the region of the examined person 11. Magnetic field gradients can produce a spatial coding of the effectiveness of radio-frequency pulses that produce the resonance condition of the spin systems.

The basic magnetic field generated by the magnet 10 polarizes the spin system in the first slice 51 and the second slice 52. In their idle state, the spins point along the direction of the basic magnetic field. Via the radio-frequency coils 15a and 15b, a radio-frequency pulse can be generated that deflects the magnetization out of its idle state in the basic magnetic field. A radio-frequency generator 20 is provided to apply radio-frequency pulses by means of the radio-frequency coils 15a, 15b. Furthermore, a magnetization signal that inductively produces a voltage in the radio-frequency coils 15a, 15b can be detected and supplied to a computer 22. A gradient unit 23 is provided in order to control the gradient system 14 to apply magnetic field gradients. A pulse sequence controller 21 controls the chronological sequence of the radio-frequency pulses that are generated via radio-frequency generator 20 and the magnetic field gradients that are controlled via gradient unit 23. An operating unit is connected with the control elements and allows a user to implement the control of the magnetic resonance system 30. In particular, computer 22 can control the radio-frequency coils 15a, 15b such that sufficient MR data are acquired in order to generate a complete data set by means of a suitable algorithm. Methods of parallel imaging (for example SMASH, GRAPPA or SENSE) are known those skilled in the art for this purpose.

Furthermore, gradient unit 23 controls the gradient system 14 such that nonlinear magnetic field gradients are generated. The radio-frequency generator 20 furthermore configure the radio-frequency pulses (that are applied via radio-frequency coils 15a, 15b) such that they furthermore define a spatial phase response in addition to a spatial amplitude dependency. For example, this can be achieved by means of suitable amplitudes or, respectively, phase modulation of the RF pulses.

The general functionality of an MR system is known to those skilled in the art, such that a more detailed description of the general components is omitted.

Figure 2:
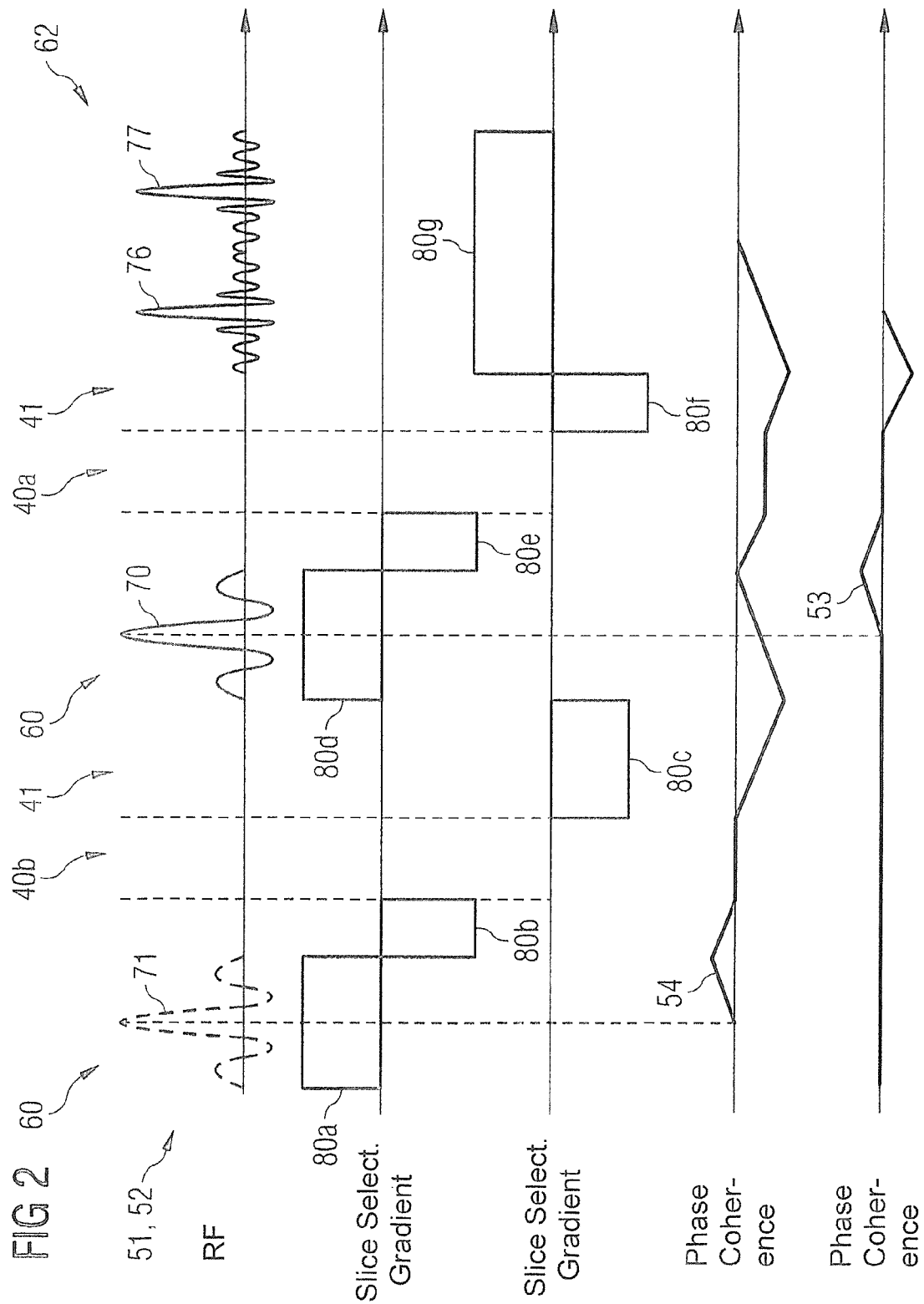
FIG. 2 schematically shows a slice multiplexing measurement sequence for slice-specific detection of incorrect MR data.

A slice multiplexing measurement sequence is schematically presented in FIG. 2. The measurement sequence presented in FIG. 2 enables the acquisition of MR data for a first slice 51 and a second slice 52. Radio-frequency excitation pulses 70, 71 are applied to deflect the magnetizations of the first and second slice 51, 52 respectively out of their idle state. The frequencies of the radio-frequency excitation pulses 70, 71 are matched to the switched gradient fields 80a and 80d such that respectively only the magnetization of the first slice (for the first excitation pulse 70) or of the second slice (for the second excitation pulse 71) are deflected out of the idle state during the excitation step 60. The second radio-frequency pulse 71 is depicted with a dashed line and occurs chronologically before the first radio-frequency pulse 70.

The coherence curves of the first slice (the coherence curve 53) and of the second slice (the second coherence curve 54) are presented in the lower part of FIG. 2. Since the deflection of the magnetization of the first slice out of the idle state happens at a later point in time than the deflection of the magnetization out of the idle state of the second slice, the first coherence curve 53 only has a phase evolution at a later point in time. In contrast to this, the signal 76 of the first slice 51 is detected before the signal 77 of the second slice 52. The measurement sequence shown in FIG. 2 is a gradient echo measurement sequence. The signals 76, 77 occur at points in time at which the first and second coherence curve 53, 54 exhibit a disappearing dephasing. However, as is clear from FIG. 2 the magnetizations of both slices 51, 52 are affected simultaneously at at least one point in time (for example during the application of the gradient field 80*f*).

The time separation of the excitation pulses 70, 71 during the excitation step 60 and the time separation of the signals 76, 77 during the detection step 62 are characteristic properties of a simultaneous echo refocusing measurement sequence as it has already been explained in detail above.

It is now possible to acquire signal from only the first slice during a correction data acquisition step. This is in particular the case since the second coherence curve 54 exhibits a dephasing during the correction data acquisition step 40*a*. This means that no corresponding signal can be detected due to the destructive interference of the various spins of the second slice. Graphically, this is illustrated by a final interval of the second coherence curve 54 from the reference axis during the correction data acquisition step 40*a*. It is then possible to acquire data that relate only to the first slice 51 during the correction data acquisition step 40*a*.

Such data can be used to correct phase errors, for example. Since such phase errors are typically segment-dependent and therefore are slice-specific, it is necessary that MR signals from only the first slice are acquired during the correction data acquisition step 40*a*.

As is clear from FIG. 2, the dephasing of the second coherence curve 54 during the correction data acquisition step 40*a* is ensured via the application of a correction assistance step 41 in the form of a magnetic field gradient 80*c*. Gradient field 80*c* ensures a dephasing of the magnetization of the second slice 52 along the readout gradient direction. Due to this dephasing—i.e. effectively a spoiling of the signal portions of the second slice—it is possible to detect exclusively signal of the transversal magnetization of the first slice 51, immediately after the first excitation pulse 70 of the first slice 51 during the correction data acquisition step 40*a*.

The magnetic field gradient 80*f* that is switched following the correction data acquisition step 40*a* ensures that the first and second coherence curve 53, 54 are reestablished after said correction data acquisition step 40*a* such that a detection of the first and second signal 76, 77 is possible during the readout step 62. In particular, by suitable dimensioning of the gradient field 80*f* as part of the correction assistance step 41 it must be ensured that the temporal arrangement of the signals 76, 77 is compatible with an MR acquisition sequence according to simultaneous echo refocusing.

Furthermore, from FIG. 2 it is clear that an additional correction data acquisition step 40*b* exists before deflection of the spin system of the first slice 51 out of the idle state, which means before application of the first excitation pulse 70. The correction data acquisition step 40*b* can be used in order to acquire MR data of the spin system of the second slice 52. Since no transversal magnetization is present during the correction data acquisition step 40*b* in the first slice, the spin system of the first slice 51 can also not contribute to the signal.

Figure 3:
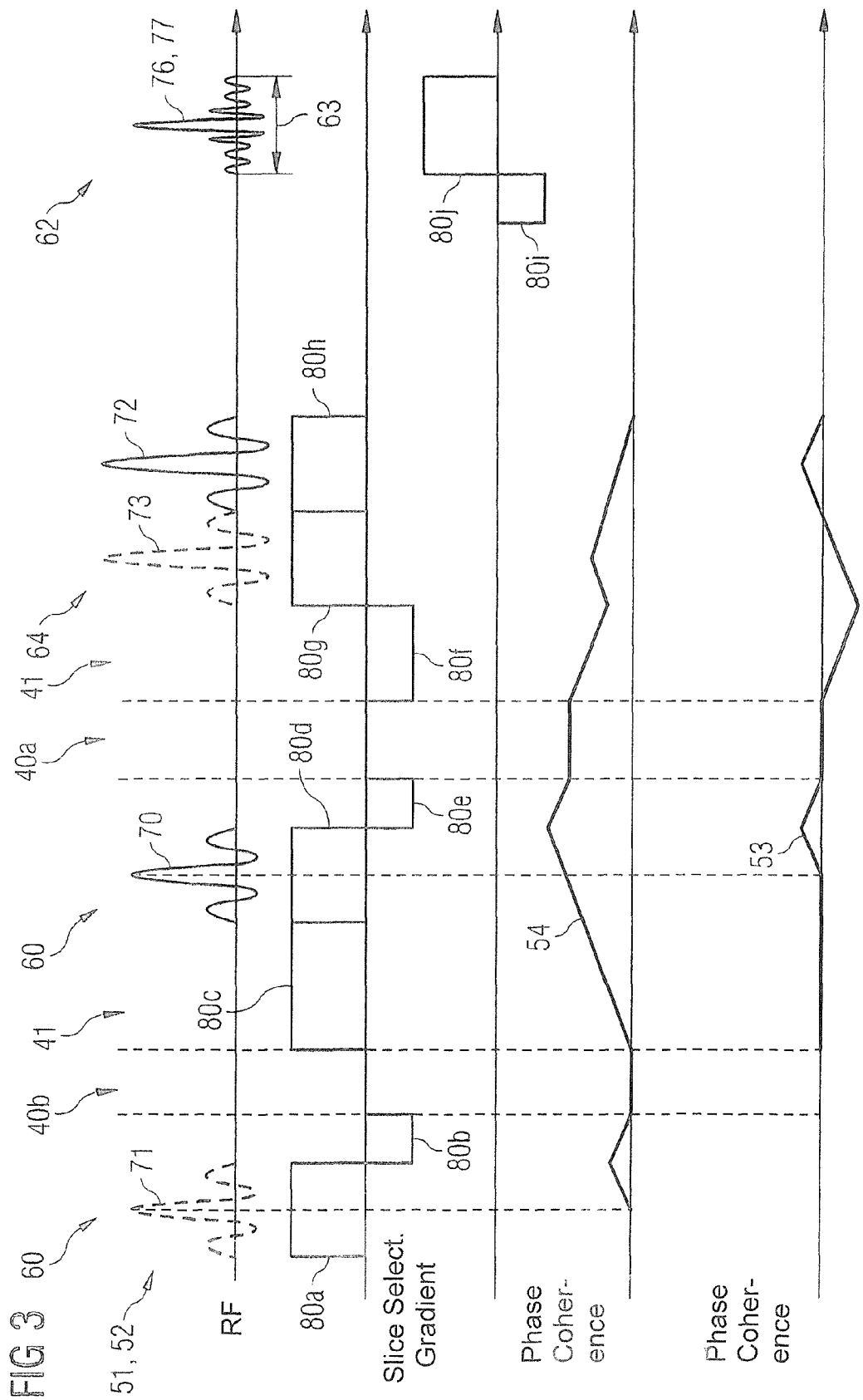
FIG. 3 schematically shows a slice multiplexing measurement sequence for slice-specific detection of incorrect MR data.

Shown in FIG. 3 is a slice multiplexing measurement sequence that, in contrast to FIG. 2, also includes the application of refocusing pulses 72, 73 during a phase modification step 64. It is thus a spin echo-like acquisition sequence (in contrast to a purely gradient-like acquisition sequence of FIG. 2). In FIG. 3 MR data of the magnetization are also acquired from a first slice 51 and a second slice 52. The magnetization of the first slice 51 is deflected out of its idle state via a first radio-frequency excitation pulse 70. The magnetization of the second slice 52 is accordingly deflected out of its idle state via a second radio-frequency excitation pulse 71. The excitation pulses occur within the scope of an excitation step 60. The second RF excitation pulse occurs temporally before the first RF excitation pulse. Various gradient fields 80*a*-80*j* are switched during the acquisition sequence, in particular in order to vary the coherence curves 53, 54 of the first and second slices 51, 52. The first coherence curve 53 of the first slice 551 is shown in the lower part of FIG. 3. Shown above this is the second coherence curve 54 of the second slice 52.

After the application of the first excitation pulse 70 or, respectively, after the application of the gradient field 80*e*, during a correction data acquisition step 40*a* the possibility exists to read out signal of the magnetization of the first slice 51. In particular, the second coherence curve 54 of the magnetization of the second slice 52 has a dephased coherence curve during the correction data acquisition step 40*a*. By the application of a gradient field 80*c* within the scope of a correction assistance step 41 before the deflection of the magnetization of the first slice out of the idle state by a first excitation pulse 70, it can be produced that the second coherence curve 54 is dephased during the correction data acquisition step 40*a*. However, after the correction data acquisition step 40*a* it must be ensured that the first and second coherence curve 53, 54 are modified such that signals 76, 77 of the magnetization of the first and second slice 51, 52 can be acquired simultaneously during a signal detection time period 62 within the scope of a readout step 62. The necessary rephasing of the coherence curves 53, 54 is achieved via suitable dimensioning of the gradient field 80*f*. Furthermore, it can be necessary to adapt the time sequence of the refocusing pulses 72, 73 (that produce a refocusing of the spin system of the first and second slices 51, 52) such that a rephasing of the coherence curves 53, 54 is possible.

While (as shown in FIG. 3) a generation of the signals 76, 77 happens via suitable switching of the magnetic field gradients 80*i* and 80*j* (dephasing, rephasing) and in particular the preceding rephasing of the coherence curves 53, 54, via suitable temporal arrangement of the excitation pulses 70, 71 in relation to the refocusing pulses 72, 73 it can additionally be possible to achieve that a spin echo condition is satisfied in addition to a gradient-like echo achieved via the gradient fields 80*i* and 80*j*: a spin echo condition is satisfied when the time period between an excitation pulse 70, 71 and a refocusing pulse 72, 73 is equal to the time period between a refocusing pulse 72, 73 and a signal 76, 77. According to the invention it is possible to enable both a rephasing of the coherence curves 53, 54 (and therefore a gradient-like signal in a readout time period 62), and to ensure the spin echo condition as was just explained.

As explained in detail with regard to FIG. 2, in an MR acquisition sequence as it is shown in FIG. 3 it is also possible to provide an additional correction data acquisition step 40*b* that enables MR data of the magnetization of the second slice 52 to be acquired. The correction data acquisition step 40*b* again takes place before the excitation pulse 70 that deflects the magnetization of the first slice 71 out of the idle state.

Figure 4:
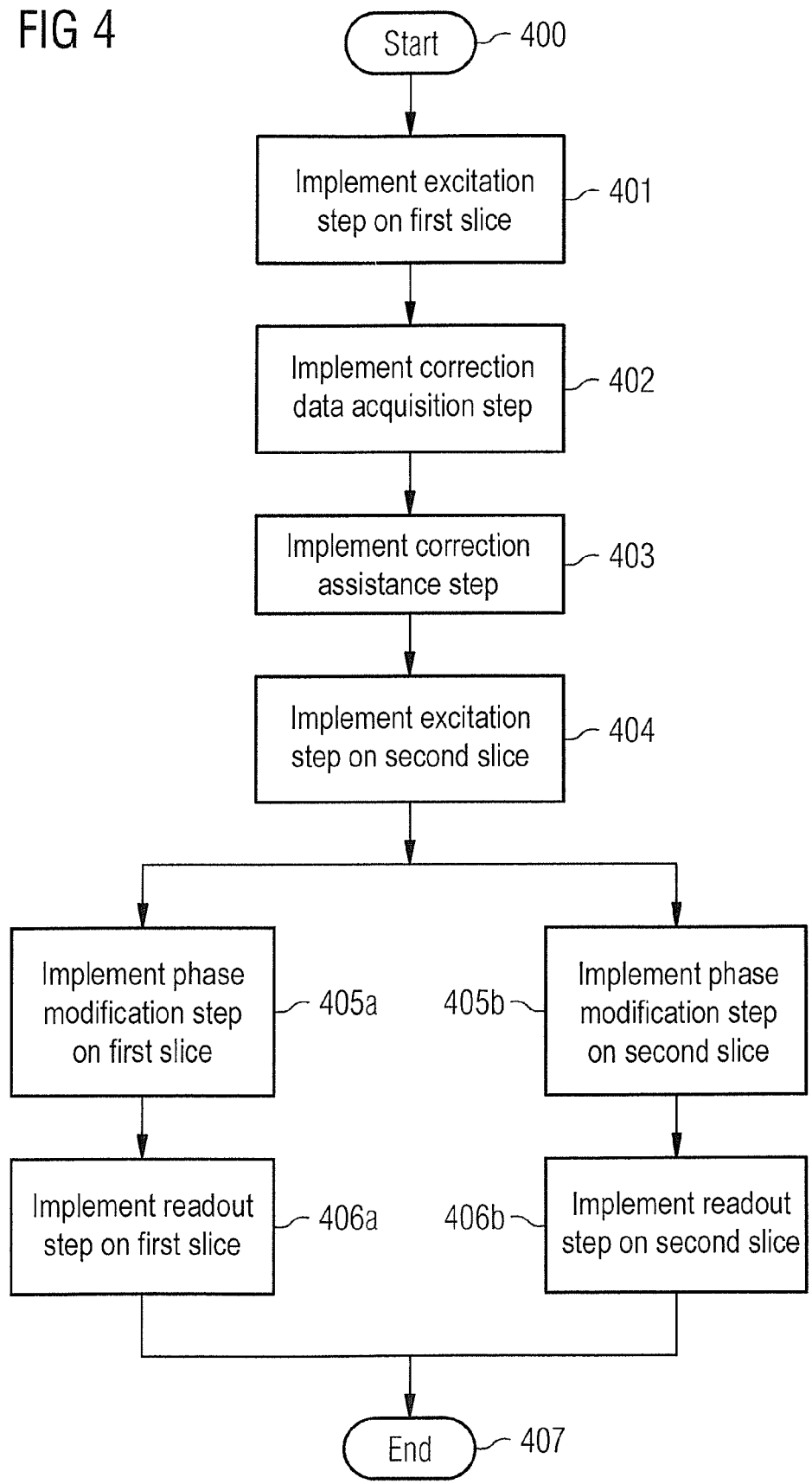
FIG. 4 is a flowchart of an embodiment of a slice multiplexing measurement sequence for slice-specific detection of incorrect MR data.

Depicted in FIG. 4 is a flow diagram to schematically illustrate a measurement sequence according to one aspect of the present invention for implementation of a correction data acquisition step for selective data acquisition of a first slice. The method begins in Step 400. First, within the scope of a first acquisition sequence in Step 401 the magnetization of a first slice is deflected out of the idle state. This takes place in the form of an excitation step that typically detects [sic] a radio-frequency excitation pulse. In a further step 402, a correction data acquisition step can be implemented that acquires signal of only the first slice. In particular, it can be the case that no additional transversal magnetization from an additional slice [sic] at the point in time of the implementation of Step 402. This is provided in the case of FIG. 4 since no additional slice was excited by an excitation pulse or, respectively, no additional acquisition sequence was started.

The implementation of a correction assistance step takes place in Step 403. The correction assistance step can have the effect that the coherence curve of the first slice is specifically modified so that, at a later point in time (during a readout step, for example), it is ensured that the coherence curve of the first slice has the correct phase position. For example, the phase position of the first slice can be adjusted within the scope of the correction assistance step 403 such that the point in time of the rephasing (and therefore the point in time of a gradient echo-like signal) is set compatible to a slice multiplexing measurement sequence.

A transversal magnetization component of the spin system of a second slice is generated in Step 404 within the scope of a second acquisition sequence. This can in turn occur via the application of an additional radio-frequency pulse whose radio-frequency is matched to the resonance condition of the second slice.

As is apparent from FIG. 4, the excitation or, respectively, deflection of the magnetizations of the first and second slice takes place sequentially. Nevertheless, specific portions of the acquisition sequence (here the following Steps 405-406) that relate to the implementation of a phase modification step and the implementation of a readout step occur in parallel. The simultaneous (at least at one point in time) action on the transversal magnetization of multiple slices is a mark of slice multiplexing measurement sequences. For example, in Step 405*a* and 405*b* the coherence curves of the first and second slice are affected in parallel, for example via the switching of suitable magnetic field gradients or suitable refocusing pulses. By the parallel implementation of Steps 405*a* and 405*b*, the advantage results that the duration that is necessary to implement the acquisition sequence according to FIG. 4 can be reduced. It is furthermore possible to acquire signal from the first slice and the second slice simultaneously in Steps 406*a* and 406*b*. The simultaneous readout of signals from multiple slices typically requires a special dependency between the coherence curves of the various slices. This special dependency—for example simultaneously disappearing dephasing—can take place by suitable implementation of the correction assistance step 403 or by suitable implementation of the phase modification steps 405*a* and 405*b*, as was presented above.

The simultaneous detection of signals from multiple slices 406*a* and 406*b* according to slice multiplexing measurement sequences can take place via a coding of the slice information, for example in frequency or phase space. Furthermore, it is possible to separate the signals of the various slices by using multiple coils arranged along a spatial direction, with knowledge of the spatial sensitivity profiles of these coils. Other measurement sequences according to slice multiplexing are based on the fact that the signals of the various slices are not detected in parallel but rather with a slight time gap. This is achieved via a targeted rephasing of the various coherence curves in succession (simultaneous spin echo refocusing).

As is apparent from preceding FIGS. 2-4, in general according to the present invention it is necessary to influence the coherence curves of the first and second slice differently to suppress a signal contribution of a second slice during a correction data acquisition step to acquire MR signals from only a first slice at at least one point in time. This is the case since it can thus be ensured that the coherence curve of the second slice advantageously has a dephased coherence curve during the correction data acquisition step while the coherence curve of the first slice has no dephasing. The different effect on the first and second coherence curves 53, 54 of the first and second slices 51, 52 can take place, for example, by measurement sequences as they have been presented with regard to FIGS. 2-4. Since the first and second slices 51, 52 are excited sequentially, the possibility exists to individually affect one of the two coherence curves between the two excitation steps 60 that relate to both slices 51, 52. This can ensure a dephasing of the corresponding coherence curve during the correction data acquisition step 40. According to the present invention, however, give complete parallelism of (for example) the excitation steps it is also possible to individually affect the coherence curves 53, 54, and furthermore to thereby ensure a dephasing of the second coherence curve 54 of the second slice 52 during the correction data acquisition step 40 of the first slice. This is presented in relation to FIGS. 5 and 6 and should be explained in detail in the following.

Radio-frequency pulses 70, 72, 74 to deflect the magnetization of the first slice 51 are applied in FIG. 5. The radio-frequency pulses 70, 72, 74 can be, for example, an excitation pulse 70, a rephasing pulse 72 or a diffusion refocusing pulse 74 for diffusion-coded MR imaging. Respective second radio-frequency pulses 71, 73, 75 for deflection of the spin system of the second slice 52 are applied simultaneously with the respective first radio-frequency pulses 70, 72, 74. A magnetic field gradient 80*a* acts during the application of the two radio-frequency pulses 70-75.

It is possible to design the excitation pulses 70-75 in the form of radio-frequency pulses that intrinsically impress a phase profile on the coherence curves of the first and second slice 51, 52. It is possible to design the amplitudes or, respectively, phase modulations of the radio-frequency pulses such that the rate of change of the dephasing of the coherence curves that is impressed during the application of the radio-frequency pulses 70-75 is different. This is shown at the bottom in FIG. 5. There it is clear that the temporal evolution of the first coherence curve 53 runs differently than the temporal evolution of the second coherence curve 54 during the application of the radio-frequency pulses. In particular, the first coherence curve 53 has a smaller change of the dephasing as a function of time than the second coherence curve 54. This has the effect that a correction magnetization phase 65 is present after the end of the excitation process, meaning after the end of the gradient field 80*b*. During a subsequent correction data acquisition step 40 (not shown in FIG. 5), the correction magnetization phase 65 is now suitable to ensure that the second coherence curve 54 has a dephasing while the first coherence curve 53 has no dephasing. According to FIG. 5 this is easily achieved since a phase difference 65 between the two coherence curves 53, 54 already exists after the end of the application of gradient field 80a, i.e. after the application of the RF pulses.

A high degree of parallelism in the imaging of two slices 51, 52 can thus be achieved. For example, it is possible to simultaneously implement the radio-frequency pulses 70-75 acting on different slices. This allows the measurement time required to implement the MR acquisition sequence to be reduced. In particular, this method can be combined with known methods of slice multiplexing as explained above.

While a complete temporal overlapping of the radio-frequency pulses of the first slice 70, 72, 74 with the radio-frequency pulse of the second slice 71, 73, 75 is shown in FIG. 5, it is understood that a partial temporal overlapping of the two radio-frequency pulses is also possible. A partial temporal overlap (in contrast to the complete temporal overlap) has the advantage that the required amplitude of the radio-frequency pulses can be reduced given a consistent deflection of the magnetization. This means that the required peak radio-frequency power can be reduced given a consistent signal-to-noise ratio.

Shown in FIG. 6 is an additional possibility of how a phase difference 65 between a first coherence curve 53 of the first slice 51 and a second coherence curve 54 of the second slice 52 can be achieved in an MR measurement sequence according to slice multiplexing given a high degree of parallel implementation of the imaging of said first slice 51 and said second slice 52. As is clear from FIG. 6, via suitable gradient fields 80b it is possible to achieve a different temporal evolution of the coherence curves 53, 54 of the various slices 51, 52.

For example, using multiple radio-frequency field coils with different spatial effectiveness it is possible to achieve a spatial curve of the magnetic field strength of the gradient field that is nonlinear. For example, a spatial curve of the gradient field can be achieved that is described by a quadratic function (second order polynomial). Given use of such a gradient field it is possible to dimension the parameters of the quadratic function such that the effective magnetic field gradient 80b is described well by a linear function at the location of the first slice 51 and at the location of the second slice 52. The two linear approximations of the quadratic spatial dependency of the gradient field 80b then in particular have a different strength. This has the effect that the magnetic field gradient 80b deploys a different effect at the location of the first slice 51 and at the location of the second slice 52, i.e. produces a different rate of change of the dephasing of the first and second coherence curves 53, 54. This is apparent from the bottom of FIG. 6, where the rate of change of the dephasing described by the second coherence curve 54 is greater than the rate of change of the dephasing described by the first coherence curve 53 during the application of the magnetic field gradient 80b. The second coherence curve 54 is hereby shown with a dashed line. This has the result that, after the end of the gradient field 80b, a correction magnetization phase 65 or phase difference between the first and second coherence curve 53, 54 is present. According to this embodiment of the invention, this phase difference can be used so that, during a correction data acquisition step 40 (not shown in FIG. 6) it is ensured that the second coherence curve 54 has a dephased phase while the first coherence curve 53 has no dephasing. This then enables data from only the first slice 51 to be acquired during the correction data acquisition step 40, as was explained in detail above.

In the exemplary embodiment of the present invention that is described with regard to FIG. 6 it is also possible—without reducing the parallelism of the implementation of the slice multiplexing measurement sequence, i.e. without chronologically serial action on the two slices 51, 52—to achieve that a phase difference 65 is present between the two coherence curves. With regard to a correction data acquisition step 40, this deploys the advantageous properties described above. According to a further aspect of the present invention, however, a method is also provided for slice-selective correction of incorrect MR data in slice multiplexing measurement sequences. The correction of incorrect MR data can hereby occur via the impression of a slice-specific correction magnetization phase 65. This correction magnetization phase 65 is used to specifically modify a first coherence curve 53 of a first slice 51. This is implemented such that a second coherence curve 54 of an additional (second, for example) slice 52 is not changed.

The exemplary embodiments of FIGS. 5 and 6 are also relevant with regard to this aspect of the present invention. As was explained in the preceding, the application of radio-frequency pulses of suitable amplitude and phase modulation or, respectively, the use of spatially nonlinear gradient fields enable the coherence curves of the various slices to be modified individually given parallel application of the pulses or, respectively, gradient fields. Given a completely parallel implementation of the various steps, a correction phase 65 can thereby also be impressed on the first coherence curve 63.

The impression of a correction magnetization phase 65 is relevant to the correction of Maxwell field-dependent error terms, for example. Ideally linear gradient fields are thus not a solution for the fundamental Maxwell field equations. It is therefore advantageous to take into account correction terms in the form of correction magnetization phases 65. In particular, these correction terms are dependent on the location within the measurement subject, and therefore on the measured slice.

An additional possibility to introduce a slice-specific correction magnetization phase 65 is shown in FIG. 7. A measurement sequence according to slice multiplexing is shown in which MR imaging again takes place for two slices 51, 52. In an excitation step 60 the magnetizations of the first and second slice 51, 52 are initially simultaneously deflected out of the idle state by means of the radio-frequency pulses 70, 71. Transversal magnetization is generated both in the first slice 51 and in the second slice 52. This is apparent in the lower part of FIG. 7 in that, during the excitation step 60, both the first coherence curve 532 of the first slice 51 and the second coherence curve 54 of the second slice 52 exhibit a change of the phase position as a function of time. For example, the simultaneous application of excitation pulses 70, 71 can take place as presented in detail above via a frequency or phase coding or via multiple coil elements.

While the excitation pulses 70, 71 occur simultaneously, the refocusing pulses 72, 73 are separate. The application of a second radio-frequency refocusing pulse 73 that only affects the second slice 52 initially takes place in a phase modification step 64. The application of a magnetic field gradient 80e subsequently takes place within the scope of a correction step 61. The magnetic field gradient 80e is in particular applied after the second refocusing pulse 73 but before the first refocusing pule 72 that deploys its effectiveness to the first slice 51. Therefore, the phase change of the coherence curves 51, 52 that is caused by the magnetic field gradient 80*e* exhibits different algebraic signs with regard to the first and second coherence curve. The dephasing is thus reduced in the first coherence curve 51 while the dephasing is increased in the second coherence curve 52.

Via the application of a magnetic field gradient 80*e* within the scope of a correction step 61 between the refocusing pulses of a first and second slice 51, 52 it is possible to separate the associated first and second coherence curves 53, 54. This is equivalent to the capability to impress a correction phase 65 on the first coherence curve 51. From FIG. 7 it is clear that, after application of the first refocusing pulse 72 within the scope of a phase modification step 64, the first coherence curve 51 has a correction magnetization phase 65. In contrast to this, the second coherence curve 54 has no correction magnetization phase.

In FIG. 7 the corresponding gradient fields 80*c*, 80*e* are dimensioned such that the second coherence curve 52 has a disappearing correction magnetization phase. However, this example may not be construed as limiting. In particular, it is also possible to dimension the gradient fields such that the second coherence curve also has a correction magnetization phase. For example, this is discussed in detail in the following with regard to the exemplary embodiment discussed in relation to FIG. 8.

In the following the magnetization phases $M_a$-$M_f$ are associated with the gradient fields 80*a*-80*f*. According to the acquisition sequence shown in FIG. 7, the correction magnetization phase 65 or, respectively, $M_x$ results as $M_x=M_a/2-M_b+M_c+M_d-M_e$. In contrast to this, the phase $M_y$ of the second coherence curve 54 at the point in time after the end of the application of the gradient field 80*f* results as $M_y=M_a/2-M_b+M_c+M_e-M_f$.

The correction magnetization phase 65 or, respectively, $M_x$ can be dimensioned via suitable selection of the magnetic field gradient 80*e* (and therefore of $M_e$). In particular, the dephasing of the first coherence curve 51 can be adjusted in relation to the dephasing of the second coherence curve 52 after the end of the application of the first refocusing pulse 72. The magnetic field gradient 80*c* can hereby have the effect that the second coherence curve 52 has a disappearing dephasing (i.e. $M_y=0$) at the end, and that the first coherence curve 51 has a dephasing that is equal to the correction magnetization phase 65. However, it is also possible that $M_y$ is not equal to 0.

An additional embodiment of an MR measurement sequence according to the present invention is shown in FIG. 8; this enables a first and second correction phase 65*a*, 65*b* to be respectively impressed on the first slice 51 and the second slice 52. As is apparent from the upper part of FIG. 8, the excitation of the first and second slice 51, 52 occur with time separation and sequentially. The magnetization of the first slice 51 is initially deflected out of the idle state by means of a first excitation pulse 70. Transversal magnetization is generated in the first slice. The first coherence curve 53 of the first slice simultaneously has a variation of the dephasing over time.

After the application of two magnetic field gradients 80*b* and 80*c*, the magnetization of the second slice 52 is subsequently deflected out of the idle state via an additional, second excitation pulse 71. At this point in time the second coherence curve 54 also has a dephasing. It can now be desirable to respectively provide both the first slice 51 and the second slice 52 with a correction phase 65*a* and 65*b*. According to the present invention, this is possible via suitable dimensioning of the magnetic field gradients 80*a*-80*f*, as is explained in detail in the following.

A sinc-shaped amplitude modulation of the excitation pulses 70, 71 is graphically indicated in FIG. 8. Such an amplitude modulation has the advantage that a particularly precisely defined spatial excitation profile of the magnetization can be achieved. However, it is possible to select a different form of the amplitude modulation of the excitation pulses. For example, the first and second excitation pulse 70, 71 can have an amplitude modulation that is asymmetrical relative to the point of maximum amplitude. In particular, if the asymmetry in the first excitation pulse 70 is opposite to that of the second excitation pulse 71, this can advantageously have the effect that the spin echo times of the first and second slice 51, 52 deviate less significantly within the scope of a spin echo measurement sequence in which refocusing pulses generate spin echo signals. The spin echo times are hereby defined as the time periods between the excitation of a spin system and the point in time of the occurrence of the spin echo.

The magnetic field gradients 80*a*-80*f* are respectively associated with a phase change $M_a$—Magnetic field. A longer effective or, respectively, a stronger magnetic field gradient 80 hereby results in a stronger phase change. For example, it can be desirable to impress a correction magnetization phase 65*a* on the first coherence curve 53 and a correction magnetization phase 65*b* on the second coherence curve 54. The correction magnetization phase 65*a* is quantified by a magnetization phase $M_x$: $M_x=M_a/2-M_b+M_c+M_d-M_e+M_f$. Furthermore, the correction magnetization phase 65*b* is quantified by a magnetization phase $M_y$: $M_y=M_a/2-M_e+M_f$. From these two equations, the dimensioning of the gradient fields 80*c* and 80*f* can be determined by the following equations: $M_c=M_x-M_y$, and $M_f=M_y$, insofar as $M_a=M_b=M_d=2M_e$, for example. The application of the magnetic field gradients 80*c* and 80*f* is accordingly associated with a first correction step 61*a* and a second correction step 61*b*. The dashed-line branch of the first coherence curve represents the curve without correction step 61*a*. As is clear, correction step 61*a* has the effect that the correction magnetization phases 65*a*, 65*b* of the first and second slice are dimensioned differently. After a correction magnetization phase has been impressed on the two slices 51, 52 (as explained using FIG. 8), the additional acquisition sequence can be continued according to a conventional slice multiplexing measurement sequences.

The exemplary embodiment discussed in the preceding with regard to FIG. 8 may not be considered to be limiting. Instead of the time separation of the excitation pulses as explained above, a time separation of refocusing pulses in spin echo measurement sequences can also be made in a corresponding manner. For example, a gradient moment $M_a$—due to a correspondingly dimensioned gradient field, for example—can be impressed between a first refocusing pulse acting on a first slice and a second refocusing pulse acting on a second slice. Furthermore, a gradient moment $M_b$ can be impressed after the second refocusing pulse. Corresponding to the above statements with regard to FIG. 8, a dependency on the first and second correction phase $M_x$ and $M_y$ can then be derived: $M_a=\frac{1}{2}(M_x-M_y)$ and $M_b=\frac{1}{2}(M_x+M_y)$. An individual correction phase can thus be impressed on the two coherence curves via suitable dimensioning of the gradient fields between and after the refocusing pulses.

In FIG. 9 a flowchart is shown that represents the workflow of a slice multiplexing measurement sequence according to an aspect of the present invention. In particular, it is shown how a correction magnetization phase can be impressed. The method begins in Step 900. A correction magnetization phase of the first slice is initially calculated in Step 901. For example, the calculation of a correction magnetization phase can take place in relation to the correction of Maxwell field terms. It is possible to implement the calculation of the correction terms given a known arrangement of the measurement geometries or, respectively, known gradient field structures in advance. The calculation of the correction magnetization phase can, for example, take place in a computer of a magnetic resonance system according to one aspect of the present invention. While only one correction magnetization phase is calculated in the embodiment shown in FIG. 9, it is also possible (for example) to calculate the correction magnetization phase for additional slices in Step 901. These could accordingly be impressed on the additional slices in a later step.

As soon as the correction magnetization phase has been calculated in Step 901, the actual measurement sequence starts with Steps 902a and 902b. The magnetization of a first and second slice is deflected out of its idle state within the scope of a first and second acquisition sequence in Steps 902a and 902b. This typically occurs by means of radio-frequency excitation pulses that generate a final transversal magnetization (i.e. a magnetization that has a component perpendicular to a static basic magnetic field).

In Step 903, a phase correction step can impress the correction magnetization phase calculated in Step 901 on the coherence curve of the spin system of the first slice. As has previously been described in connection with FIG. 5 or 6, for example, the impression of a correction magnetization phase selectively on the spin system of the first slice can occur via the use of nonlinear gradient fields or specific amplitude-modulated radio-frequency pulses, for example. However, via clever temporal arrangement of gradient fields that have a linear spatial curve it is also possible to respectively achieve, within the scope of the first and second acquisition sequence in relation to the excitation or, respectively, refocusing pulses of the first and second slice, that the coherence curves of said first and second slice have a different temporal evolution, and therefore that a correction phase can be impressed on the first slice. This was explained in detail using FIGS. 7 and 8.

After a correction magnetization phase has been impressed in a phase correction step in Step 903, in Steps 904a-905b a slice multiplexing MR measurement sequence can be further implemented in connection with phase modification and readout steps. These steps correspond to Steps 405a-406b that were described in connection with FIG. 4. The method ends in Step 906.

Although modifications and changes may be suggested by those skilled in the art, it is the intention of the inventor to embody within the patent warranted hereon all changes and modifications as reasonably and properly come within the scope of his contribution to the art.

I claim as my Invention:

1. A method configured for detecting and correcting magnetic resonance (MR) image data, comprising:
   with a control computer, operating an MR data acquisition unit with a first acquisition sequence in order to acquire MR data from a first slice of a subject, and in order to generate a basic magnetic field having a basic field direction, said first acquisition sequence producing a magnetization of nuclear spins in said first slice where the produced magnetization occurs in a plane that is transverse to the basic field direction and in which the produced magnetization has a phase that exhibits a phase evolution represented as a first coherence curve;
   with a control computer, operating said MR data acquisition unit in order to acquire MR data from a second slice of the subject, said second acquisition sequence producing a magnetization of nuclear spins in said second slice where the produced magnetization in the second slice occurs in another plane that is transverse to the basic field direction and in which the produced magnetization has a phase that exhibits a phase evolution represented as a second coherence curve, wherein said first acquisition sequence and said second acquisition sequence are at least partially temporally overlapping so that said magnetization of said nuclear spins in said first slice and said magnetization of said nuclear spins in said second slice occur simultaneously at, at least one point in time, in which the overlapping occurs;
   with a control computer, operating said MR data acquisition unit with a slice-selective correction data acquisition step in order to acquire MR signals from only said first slice, thereby obtaining correction data;
   with a control computer, operating said MR data acquisition unit in order to implement at least one correction assistance step that suppresses a signal contribution of said second slice that occurs during said slice-selective correction data acquisition step, and that reestablishes said first and second coherence curves after said correction data acquisition step; and
   from said control computer, making said MR data acquired from said first slice in said first acquisition sequence and said MR data acquired from said second slice from said second acquisition sequence, and said correction data, available in electronic form in order to permit further correction processing when desired.

2. A method as claimed in claim 1 comprising, in said slice-selective correction assistance step, operating said MR data acquisition unit in order to emit gradient fields that impose a correction assistance phase that then causes said second coherence curve to be dephased during said correction data acquisition step.

3. A method as claimed in claim 2 comprising generating said gradient fields with a non-linear spatial curve that makes said slice-selective correction assistance phase slice-specific for said second slice.

4. A method as claimed in claim 1 comprising, in said slice-selective correction assistance step, operating said MR data acquisition unit with a control computer, in order to radiate at least one radio-frequency pulse that imposes a slice-selective correction assistance phase by a modulation of said at least one radio-frequency pulse selected from the group consisting of amplitude modulation and phase modulation.

5. A method as claimed in claim 1 comprising with a control computer, operating said MR data acquisition unit in each of said first and second acquisition sequences in order to include an excitation step wherein said magnetization in the respective first and second slices is deflected out of an idle state, a phase modification step wherein the respective magnetization in the first and second slices is dephased and rephased, and a readout step in which a signal resulting from the respective magnetization in the first and second slices is detected within a signal detection time period.

6. A method as claimed in claim 5 comprising, in at least one of said excitation step and said phase modification step in each of said first and second acquisition sequences, radiating a radio-frequency pulse with said MR data acquisition unit.

7. A method as claimed in claim 5 comprising operating said MR data acquisition unit in order to implement said excitation step in said first acquisition sequence, and said slice-selective correction data acquisition step, before the excitation step of said second acquisition sequence.

8. A method as claimed in claim 5 comprising with a control computer, operating said MR data acquisition unit in order to implement said excitation step of said first acquisition sequence, and said slice-selective correction data acquisition step, after said excitation step of said second acquisition sequence, and in order to implement said slice-selective correction assistance step and thereby cause dephasing of said signal of said second slice before said slice-selective correction data acquisition step, and wherein said slice-selective correction assistance step rephases the respective signals from the first and second slices after said correction data acquisition step.

9. A method as claimed in claim 5 comprising with a control computer, operating said MR data acquisition unit with each of said first and second acquisition sequences being a simultaneous echo refocusing sequence, and with a control computer, implementing the respective readout steps in said respective simultaneous echo focusing sequences with a time offset in said signal detection time period.

10. A method as claimed in claim 5 comprising with a control computer, implementing the respective readout steps in said first and second acquisition sequences simultaneously within said signal detection time period.

11. A method as claimed in claim 10 comprising with a control computer, operating said MR data acquisition unit in order to implement the respective excitation steps of said first and second acquisition sequences with at least a partial temporal overlap, and differentiating respective signals from the respective first and second slices by phase or frequency.

12. A method as claimed in claim 10 comprising with a control computer, operating said MR data acquisition unit in said first and second acquisition sequences by radiating respective radio-frequency pulses from respective, multiple radio-frequency coils of said MR data acquisition unit.

13. A method as claimed in claim 10 comprising with a control computer, operating the MR data acquisition unit in order to implement the respective excitation steps of said first and second acquisition sequences with a time offset with respect to each other.

14. A method as claimed in claim 10 comprising with a control computer, operating the MR data acquisition unit in order to implement the respective phase modification steps of said first and second acquisition sequences with a time offset with respect to each other.

15. A magnetic resonance (MR) system comprising:
an MR data acquisition unit;
a control unit configured to operate said MR data acquisition unit with a first acquisition sequence in order to acquire MR data from a first slice of a subject and in order to generate a basic magnetic field having a basic field direction, said first acquisition sequence producing a magnetization of nuclear spins in said first slice where the produced magnetization occurs in a plane that is transverse to the basic field direction and in which the produced magnetization has a phase that exhibits a phase evolution represented as a first coherence curve;
said control unit being configured to operate said MR data acquisition unit in order to acquire MR data from a second slice of the subject, said second acquisition sequence producing a magnetization of nuclear spins in said second slice where the produced magnetization in the second slice occurs in another plane that is transverse to the basic field direction and in which the produced magnetization has a phase that exhibits a phase evolution represented as a second coherence curve, said first acquisition sequence and said second acquisition sequence at least partially temporally overlapping so that said magnetization of said nuclear spins in said first slice and said magnetization of said nuclear spins in said second slice occur simultaneously at at least one point in time in which the overlapping occurs;
said control unit being configured to operate said MR data acquisition unit with a slice-selective correction data acquisition step in order to acquire MR signals from only said first slice, thereby obtaining correction data;
said control unit being configured to operate said MR data acquisition unit in order to implement at least one slice-selective correction assistance step that suppresses a signal contribution of said second slice that occurs during said slice-selective correction data acquisition step, and that reestablishes said first and second coherence curves after said slice-selective correction data acquisition step; and
a processor configured to make said MR data acquired from said first slice in said first acquisition sequence and said MR data acquired from said second slice from said second acquisition sequence, and said slice-selective correction data, available in electronic form in order to permit further correction processing when desired.

16. A magnetic resonance system as claimed in claim 15 wherein said control unit is configured to, in said slice-selective correction assistance step, operate said MR data acquisition unit to emit gradient fields that impose a correction assistance phase that then causes said second coherence curve to be dephased during said slice-selective correction data acquisition step.

17. A magnetic resonance system as claimed in claim 16 wherein said control unit is configured to operate said MR data acquisition unit in order to generate said gradient fields with a non-linear spatial curve that makes said slice-selective correction assistance phase slice-specific for said second slice.

18. A magnetic resonance system as claimed in claim 15 wherein said control unit is configured to, in said slice-selective correction assistance step, operate said MR data acquisition unit in order to radiate at least one radio-frequency pulse that imposes a slice-selective correction assistance phase by a modulation of said at least one radio-frequency pulse selected from the group consisting of amplitude modulation and phase modulation.

19. A magnetic resonance system as claimed in claim 15 wherein said control unit is configured to operate said MR data acquisition unit in each of said first and second acquisition sequences, and to include an excitation step wherein said magnetization in the respective first and second slices is deflected out of an idle state, a phase modification step wherein the respective magnetization in the first and second slices is dephased and rephased, and a readout step in which a signal resulting from the respective magnetization in the first and second slices is detected within a signal detection time period.

20. A magnetic resonance system as claimed in claim 19 wherein said control unit is configured to operate said MR data acquisition unit in order to, in at least one of said excitation step and said phase modification step in each of said first and second acquisition sequences, radiate a radio-frequency pulse in said MR data acquisition unit.

21. A magnetic resonance system as claimed in claim 19 wherein said control unit being configured to operate said MR data acquisition unit in order to implement said excitation step in said first acquisition sequence, and said slice-selective correction data acquisition step, before the excitation step of said second acquisition sequence.

22. A magnetic resonance system as claimed in claim 19 wherein said control unit is configured to operate said MR data acquisition unit in order to implement said excitation step of said first acquisition sequence, and said slice-selective correction data acquisition step, after said excitation step of said second acquisition sequence, and in order to implement said slice-selective correction assistance step to thereby cause dephasing of said signal of said second slice before said slice-selective correction data acquisition step, and wherein said slice-selective correction assistance step rephases the respective signals from the first and second slices after said slice-selective correction data acquisition step.

23. A magnetic resonance system as claimed in claim 19 wherein said control unit is configured to operate said MR data acquisition unit with each of said first and second acquisition sequences being a simultaneous echo refocusing sequence, and in order to implement the respective readout steps in said respective simultaneous echo focusing sequences with a time offset in said signal detection time period.

24. A magnetic resonance system as claimed in claim 19 wherein said control unit is configured to implement the respective readout steps in said first and second acquisition sequences simultaneously in said signal detection time period.

25. A magnetic resonance system as claimed in claim 24 said control unit is configured to operate said MR data acquisition unit in order to implement the respective excitation steps of said first and second acquisition sequences with at least a partial temporal overlap, and in order to differentiate respective signals from the respective first and second slices by phase or frequency.

26. A magnetic resonance system as claimed in claim 24 wherein said control unit is configured to operate said MR data acquisition unit in said first and second acquisition sequences by radiating respective radio-frequency pulses from respective, multiple radio-frequency coils of said MR data acquisition unit.

27. A magnetic resonance system as claimed in claim 24 wherein said control unit is configured to operate the MR data acquisition unit in order to implement the respective excitation steps of said first and second acquisition sequences with a time offset with respect to each other.

28. A magnetic resonance system as claimed in claim 24 wherein said control unit is configured to operate the MR data acquisition unit in order to implement the respective phase modification steps of said first and second acquisition sequences with a time offset with respect to each other.

29. A method of detecting and correcting slice multiplexed magnetic resonance (MR) image data, comprising:
with a control computer, operating an MR data acquisition unit with a first acquisition sequence in order to acquire MR data from a first slice of a subject and in order to generate a basic magnetic field having a basic field direction, said first acquisition sequence producing a magnetization of nuclear spins in said first slice where the produced magnetization occurs in a plane that is transverse to the basic field direction and in which the produced magnetization has a phase that exhibits a phase evolution represented as a first coherence curve;
with said control computer, operating said MR data acquisition unit in order to acquire MR data from a second slice of the subject, said second acquisition sequence producing a magnetization of nuclear spins in said second slice where the produced magnetization in the second slice occurs in another plane that is transverse to the basic field direction and in which the produced magnetization has a phase that exhibits a phase evolution represented as a second coherence curve, said first acquisition sequence and said second acquisition sequence at least partially temporally overlapping so that said magnetization of said nuclear spins in said first slice and said magnetization of said nuclear spins in said second slice occur simultaneously, at at least one point in time in which the overlapping occurs;
with the control computer, operating said MR data acquisition unit in order to implement a slice-selective correction step in order to impress a slice-specific magnetization phase that modifies only said first coherence curve, while maintaining said second coherence curve; and
with the control computer, making said MR data acquired from said first slice in said first acquisition sequence and said MR data acquired from said second slice from said second acquisition sequence, after implementing said slice-selective correction step, available in electronic form in order to permit further correction processing when desired.

30. A method as claimed in claim 29 comprising with the control computer, operating said MR data acquisition unit in each of said first and second acquisition sequences in order to include an excitation step wherein said magnetization in the respective first and second slices is deflected out of an idle state, a phase modification step wherein the respective magnetization in the first and second slices is dephased and rephased, and a readout step in which a signal resulting from the respective magnetization in the first and second slices is detected within a signal detection time period.

31. A method as claimed in claim 30 comprising with the control computer, operating said MR data acquisition unit with each of said first and second acquisition sequences being a simultaneous echo refocusing sequence, and then implementing with the control computer, the respective readout steps in said respective simultaneous echo focusing sequences with a time offset in said signal detection time period.

32. A method as claimed in claim 31 comprising with the control computer, operating said MR data acquisition unit in order to implement the respective excitation steps of said first and second acquisition sequences with at least a partial temporal overlap, and then differentiating respective signals from the respective first and second slices by phase or frequency.

33. A method as claimed in claim 31 comprising with the control computer, operating said MR data acquisition unit in said first and second acquisition sequences by radiating respective radio-frequency pulses from respective, multiple radio-frequency coils of said MR data acquisition unit.

34. A method as claimed in claim 30 comprising with the control computer, operating said magnetic resonance data acquisition unit whereby the respective excitation steps in said first and second acquisition sequences are at least partially temporarily overlapping one another.

35. A method as claimed in claim 30 comprising with the control computer, implementing said at least one slice-selective correction step by radiating a radio-frequency pulse that deflects said nuclear spins in said first slice with a selected amplitude modulation or phase modulation, with said correction of slice-specific magnetization phase being impressed, with the control computer, during radiation of said radio-frequency pulse.

36. A method as claimed in claim 30 comprising, in said at least one correction step, generating a gradient field with the control computer, which impresses said of slice-specific correction magnetization phase.

37. A method as claimed in claim 36 comprising generating with the control computer, said gradient field with a non-linear spatial curve, and implementing with the control computer, said correction phase to be sliced specific slice-specific with the control computer.

38. A method as claimed in claim 21 wherein said gradient field comprises a first gradient field generated with the control computer in said second acquisition sequence before a radio-frequency refocusing pulse, and a second gradient field generated with the control computer, in said second acquisition sequence after a radio-frequency refocusing pulse.

39. A method as claimed in claim 21 wherein said gradient field comprises a first gradient field generated with the control computer in said second acquisition sequence before a radio-frequency excitation pulse, and a second gradient field generated with the control computer, in said second acquisition sequence after a radio-frequency excitation pulse.

40. A method as claimed in claim 30 comprising implementing with the control computer, said excitation step for said first slice and said slice-specific correction step before implementing, with the control computer, the excitation step of the second slice.

41. A magnetic resonance (MR) system comprising:
an MR data acquisition unit;
a control unit configured to operate said MR data acquisition unit with a first acquisition sequence in order to acquire MR data from a first slice of a subject and in order to generate a basic magnetic field having a basic field direction, said first acquisition sequence producing a magnetization of nuclear spins in said first slice where the produced magnetization occurs in a plane that is transverse to the basic field direction and in which the produced magnetization has a phase that exhibits a phase evolution represented as a first coherence curve;
said control unit being configured to operate said MR data acquisition unit in order to acquire MR data from a second slice of the subject, said second acquisition sequence producing a magnetization of nuclear spins in said second slice where the produced magnetization in the second slice occurs in another plane that is transverse to the basic field direction and in which the produced magnetization has a phase that exhibits a phase evolution represented as a second coherence curve, said first acquisition sequence and said second acquisition sequence at least partially temporally overlapping so that said magnetization of said nuclear spins in said first slice and said magnetization of said nuclear spins in said second slice occur simultaneously, at at least one point in time in which the overlapping occurs;
said control unit being configured to operate said MR data acquisition unit and implement a correction step that impresses a slice-specific magnetization phase that modifies only said first coherence curve, while maintaining said second coherence curve; and
a processor configured to make said MR data acquired from said first slice in said first acquisition sequence and said MR data acquired from said second slice from said second acquisition sequence, after said correction step, available in electronic form in order to permit further correction processing when desired.

* * * * *